United States Patent
Laser et al.

(10) Patent No.: US 9,995,412 B2
(45) Date of Patent: Jun. 12, 2018

(54) LONG-THROW MICROFLUIDIC ACTUATOR

(71) Applicant: Wave 80 Biosciences, Inc., San Francisco, CA (US)

(72) Inventors: Daniel Laser, San Francisco, CA (US); Amy Droitcour, San Francisco, CA (US); Hailemariam Negussie, San Francisco, CA (US); Radu Raduta, San Francisco, CA (US); Jared Frey, San Francisco, CA (US)

(73) Assignee: Wave 80 BioSciences, Inc., San Francisco, CA (US)

( * ) Notice: Subject to any disclaimer, the term of this patent is extended or adjusted under 35 U.S.C. 154(b) by 52 days.

(21) Appl. No.: 14/771,636

(22) PCT Filed: Feb. 28, 2014

(86) PCT No.: PCT/US2014/019590
§ 371 (c)(1),
(2) Date: Aug. 31, 2015

(87) PCT Pub. No.: WO2014/134533
PCT Pub. Date: Sep. 4, 2014

(65) Prior Publication Data
US 2016/0010761 A1 Jan. 14, 2016

Related U.S. Application Data

(60) Provisional application No. 61/771,694, filed on Mar. 1, 2013.

(51) Int. Cl.
*F16K 99/00* (2006.01)
*B01L 3/00* (2006.01)
(Continued)

(52) U.S. Cl.
CPC ...... *F16K 99/0051* (2013.01); *B01F 11/0071* (2013.01); *B01F 13/0059* (2013.01);
(Continued)

(58) Field of Classification Search
CPC .. F16K 99/051; F16K 99/17; F16K 2009/008; F16K 2009/0086;
(Continued)

(56) References Cited

U.S. PATENT DOCUMENTS 5,965,001 A 10/1999 Chow et al.
6,277,257 B1 8/2001 Paul et al.
(Continued)

FOREIGN PATENT DOCUMENTS

EP 0816837 A1 1/1998

OTHER PUBLICATIONS

PCT International Search Report and Written Opinion, PCT Application No. PCT/US2014/019590, dated Jun. 5, 2014, 18 pages.
(Continued)

*Primary Examiner* — Jayne L Mershon
(74) *Attorney, Agent, or Firm* — Fenwick & West LLP

(57) ABSTRACT

A microfluidic device includes a three-dimensional slat structure having a plurality of interstices configured to generate a high power, high flow rate of fluids by electroosmotic flow. The microfluidic device includes a housing for holding and moving fluids through the slat structure, and a plurality of electrodes that generate an electric field within the plurality of interstices.

49 Claims, 25 Drawing Sheets

(51) Int. Cl.
G01N 1/30 (2006.01)
C12Q 1/68 (2018.01)
C12N 15/10 (2006.01)
C12Q 1/02 (2006.01)
G01N 21/64 (2006.01)
G01N 33/543 (2006.01)
B01F 11/00 (2006.01)
B01F 13/00 (2006.01)
B82Y 30/00 (2011.01)

(52) U.S. Cl.
CPC ..... *B01L 3/50273* (2013.01); *B01L 3/502738* (2013.01); *B82Y 30/00* (2013.01); *C12N 15/1006* (2013.01); *C12N 15/1013* (2013.01); *C12Q 1/02* (2013.01); *C12Q 1/6806* (2013.01); *C12Q 1/6844* (2013.01); *C12Q 1/6846* (2013.01); *F16K 99/0017* (2013.01); *G01N 1/30* (2013.01); *G01N 21/6428* (2013.01); *G01N 33/54366* (2013.01); *B01L 3/502784* (2013.01); *B01L 2200/0647* (2013.01); *B01L 2200/12* (2013.01); *B01L 2300/0645* (2013.01); *B01L 2300/0654* (2013.01); *B01L 2300/0816* (2013.01); *B01L 2300/0858* (2013.01); *B01L 2300/0864* (2013.01); *B01L 2300/0867* (2013.01); *B01L 2300/12* (2013.01); *B01L 2400/0418* (2013.01); *B01L 2400/0478* (2013.01); *B01L 2400/0487* (2013.01); *F16K 2099/008* (2013.01); *F16K 2099/0084* (2013.01); *F16K 2099/0086* (2013.01); *F16K 2099/0094* (2013.01); *F16K 2099/0096* (2013.01); *G01N 2021/6432* (2013.01); *G01N 2021/6439* (2013.01)

(58) Field of Classification Search
CPC ..... F16K 2009/0094; F16K 2009/0096; H01L 2300/0858; H01L 2300/12; H01L 2400/0418; H01L 2200/12
See application file for complete search history.

(56) References Cited

U.S. PATENT DOCUMENTS

| | | | |
|---|---|---|---|
| 6,391,622 B1 | 5/2002 | Knapp et al. | |
| 2002/0179445 A1 | 12/2002 | Alajoki et al. | |
| 2004/0241004 A1 | 12/2004 | Goodson et al. | |
| 2005/0034990 A1 | 2/2005 | Crooks et al. | |
| 2005/0233198 A1* | 10/2005 | Nuzzo | H01M 4/8605 204/432 |
| 2007/0170062 A1 | 7/2007 | Lauks | |
| 2009/0155877 A1* | 6/2009 | Iliescu | B01L 3/502707 435/173.7 |
| 2009/0253196 A1* | 10/2009 | Ikeya | B01L 3/50855 435/288.4 |
| 2011/0000560 A1 | 1/2011 | Miller et al. | |
| 2011/0114492 A1 | 5/2011 | Anex et al. | |

OTHER PUBLICATIONS

PCT Written Opinion of the International Preliminary Examining Authority, PCT Application No. PCT/US2014/019590, dated May 8, 2015, 5 pages.
Zeng, S. et al., "Electroosmotic Flow Pumps with Polymer Frits," Sensors and Actuators B: Chemical, Feb. 2002, pp. 209-212, vol. 82, No. 2-3.
Yao, S. et al., "Porous Glass Electroosmotic Pumps: Theory," Journal of Colloid and Interface Science, Dec. 2003, pp. 133-142, vol. 268, No. 1.
Chen, C-H. et al., "A Planar Electroosmotic Micropump," Journal of Microelectromechanical Systems, Dec. 2002, pp. 672-683, vol. 11, No. 6.
Yao, S. et al., "Electroosmotic Pumps Fabricated From Porous Silicon Membranes," Journal of Microelecromechanical Systems, Jun. 2006, pp. 717-728, vol. 15, No. 3.
Burgreen, D. et al., "Electrokinetic Flow in Ultrafine Capillary Slits1," The Journal of Physical Chemistry, 1964, pp. 1084-1091, vol. 68, No. 5.
Laser, D.J., "Temporal Modulation of Electroosmotic Micropumps," Proceedings of IMECE 2006, 2006 ASME International Mechanical Engineering Congress and Exposition, Fluids Engineering in Micro- and Nano-Systems VII, 2006, p. 67-72.
Frey, J. et al., "Modeling Electric Fields in Slit Capillary Array Fluidic Actuators with Complex Electrode Geometrics," presented at the COMSOL User Conference, 2012, 4 pages.
Laser, D.J. et al., "Silicon Electroosmotic Micropumps for Integrated Circuit Thermal Management," The 12$^{th}$ International Conference on Solid-State Sensors, Actuators and Microsystems (Transducers '03), IEEE, Jun. 8-12, 2003, pp. 151-154.
European Extended Search Report, European Application No. 14761250.1, dated Jul. 26, 2016, 10 pages.
PCT International Search Report and Written Opinion, PCT Application No. PCT/US2014/020029, 25 pages.

\* cited by examiner

| | Flow Rate (0-60 sec) | | |
|---|---|---|---|
| | No coil | 20cm | 40cm |
| Wafer 1 Section 1 Chip 3 | 348.652 | 189.983 | 95.0189 |
| Wafer 1 Section 3 Chip 3 | 363.074 | 166.12 | 83.4783 |
| Wafer 2 Section 3 Chip 3 | 428.862 | 239.167 | 138.945 |
| Wafer 2 Section 1 Chip 3 | 519.152 | 210.242 | 98.2054 |
| Wafer 3 Section 2 Chip 2 | 294.379 | 164.515 | 96.0731 |
| Wafer 3 Section 3 Chip 3 | 419.342 | 233.006 | 131.322 |

| | Power (0-60 sec) | | |
|---|---|---|---|
| | No coil | 20cm | 40cm |
| Wafer 1 Section 1 Chip 3 | 0.136703531 | 0.102590169 | 0.224068329 |
| Wafer 1 Section 3 Chip 3 | 0.265202704 | 0.340016031 | 0.516196993 |
| Wafer 2 Section 3 Chip 3 | 0.107442925 | 0.071677871 | 0.061156910 |
| Wafer 2 Section 1 Chip 3 | 0.111770983 | 0.177467861 | 0.307062338 |
| Wafer 3 Section 2 Chip 2 | 0.11738273 | 0.163166862 | 0.353774049 |
| Wafer 3 Section 3 Chip 3 | 0.105641589 | 0.095571809 | 0.122236939 |

| Power (0-60 sec) | | | std flow | | | std power | | |
|---|---|---|---|---|---|---|---|---|
| No coil | 20cm | 40cm | No coil | 20cm | 40cm | No coil | 20cm | 40cm |
| 0.136703531 | 0.10259 | 0.224068 | 13.7457 | 8.6455 | 10.1057 | 0.00017 | 0.000169 | 0.13289 |
| 0.265202704 | 0.340016 | 0.516197 | 66.7069 | 11.2038 | 1.47186 | 0.01703 | 0.004335 | 0.103726 |
| 0.107442925 | 0.071678 | 0.061157 | 40.9228 | 15.3615 | 8.78573 | 0.00102 | 0.047853 | 0.000102 |
| 0.111770983 | 0.177468 | 0.307062 | 13.4624 | 5.9775 | 7.27613 | 0.00407 | 0.000793 | 0.237943 |
| 0.11738273 | 0.163167 | 0.353774 | 73.5381 | 7.45249 | 7.97502 | 0.00024 | 0.006536 | 0.005511 |
| 0.105641589 | 0.095572 | 0.122237 | 46.1495 | 27.3022 | 3.91234 | 0.00105 | 0.000162 | 0.012352 |

FIG. 11

Electrostatic images in COMSOL showing the 1x4mm and 2x4mm slit area as well as a mesh distribution. Clockwise from bottom left: Single wire 1x4mm area, double wire 2x4mm area, quadruple wire 2x4mm area and quad wire mesh distribution.

LONG-THROW MICROFLUIDIC ACTUATOR

CROSS REFERENCE TO RELATED APPLICATIONS

This application claims the benefit of U.S. Provisional Application No. 61/771,694, filed on Mar. 1, 2013, which is hereby incorporated in its entirety by reference.

This application is related to U.S. Provisional Application No. 61/771,708, filed on Mar. 1, 2013, which is hereby incorporated in its entirety by reference.

STATEMENT REGARDING FEDERALLY SPONSORED RESEARCH OR DEVELOPMENT

This invention was made with government support under NIH contract HHSN272200900029C and NIH grant 2R44AI073221, awarded by the National Institutes of Health. The government has certain rights in the invention.

BACKGROUND OF THE INVENTION

Field of the Invention

The invention relates to microfluidic actuators for the pressurization, transport, mixing, and other processing of small volumes of liquid.

Description of the Related Art

Microfluidic actuators are small components—typically less than 1 cubic centimeter in displaced volume—that, while functionally similar to conventional hydraulic, electrohydraulic, and pneumatic actuators [1], typically employ design and operational principles specific to their comparatively small size. Microfluidic actuators may be categorized as mechanical or non-mechanical. Mechanical microfluidic actuators use moving diaphragms or other surfaces in a continuous or cyclical manner to pressurize a volume of fluid, which in turn can be used to do mechanical work. While the nominal throw of a conventional actuator is determined by the length of the cylinder, the throw of a microfluidic actuator is typically determined by the working fluid pressurization system. Long-throw microfluidic actuators with moving surfaces require valves. The valve seals are susceptible to obstruction and other failure modes, making this type of actuator not ideal for long-term use where reliability is important. Microfluidic actuators with active valves are expensive to produce, whereas microfluidic actuators with passive valves are limited in generating high pressure and high flow rate capacity.

Non-mechanical microfluidic actuators use electrical, magnetic, optical, chemical, or electrochemical means to pressurize a volume of working fluid, which in turn can be used to do mechanical work. Phase-change microfluidic actuators use heat or electrochemical effects to convert a liquid phase to a gas phase; the pressure associated with the phase change can be used do work. The maximum pressure generated through the phase change is typically small, limiting the applications of these actuators.

Electroosmotic (EO) microfluidic actuators are a type of non-mechanical microfluidic actuator. EO microfluidic actuators use body forces on mobile ions in the fluid phase of the electric double layer at a fluid-solid interface [2] to pressurize a fluid. The fluid is referred to as the EO working fluid. The pressurized EO working fluid can be used to do external mechanical work, i.e. moving an external mass over some distance. Pressurization of the EO working fluid is modulated through the controlled application of electrical fields within portions of the EO working fluid. Electrostatic body forces acting on mobile ions in the fluid phase of electric double layers at interfaces within stationary, fluid-contacting solid structures create pressure gradients within the EO working fluid.

EO devices incorporate electrodes for generating electrical fields which create body forces on mobile ions of the electric double layer. Some EO devices use aqueous solutions as working fluids. When the electrodes are polarized by a battery or other electrical potential source, continuous electrical current can flow through the electrolytic system formed by the electrodes, the aqueous, and the electrical potential source. Continuous current flow can be supported by oxidation-reduction reactions at the electrode-aqueous interface and ionic charge transport within the bulk aqueous.

Because EO microfluidic actuator operation is electric double layer-dependent, the shape and composition of the fluid-contacting solid structures are primary determinants of actuator performance parameters like maximum pressure, response time, and throw. Many previously designed EO devices have incorporated EO flow generating structures of porous polymer layers and silica beads packed between frits [3]. While these designs produce high maximum pressures, they can require high operating voltages and the tortuous path for fluids through the bead bed limits power transduction as a function of apparatus volume and results in characteristically low flow rates [4], [5].

Many previously designed EO devices incorporate one or more approximately rectangular cross-section channels with the two cross-sectional dimensions on the same order. These devices generally do not generate sufficient fluid power to be useful for doing mechanical work on an external mass, either because the volumetric flow rate is limited by the small total cross-sectional area or because the pressure generation is limited by the high ratio of the cross-sectional dimensions to the electric double layer characteristic thickness.

Some previously designed EO devices incorporate one or more approximately rectangular cross-section channels with one cross-sectional dimension between 3 and 10 microns and the other cross-sectional dimension much larger [6]. These devices based on slit-like channels can generate appreciable fluid power, but are difficult to fixture and load because of the large difference in the in-plane dimensions.

Other previously designed EO microfluidic actuators have used one-dimensional arrays of long, narrow, closely spaced interstices between a series of slat-like structural elements. Some configurations have a smaller cross-sectional dimension of the interstices between 3 and 10 microns and a large cross-sectional dimension between 50 and 250 microns [7]. This configuration has the high fluid power generation capability of EO devices with one or a small number of slit-like channels described above, but can be more readily integrated with other microfluidic components. For example, these devices can be built into plastic cartridges for analyzing blood to characterize genomic material contained therein [8]. The ratio of the large cross-sectional dimension to the small cross-sectional dimension is referred to as the interstice aspect ratio; the ratio of the small to the large cross-sectional dimensions of the EO flow area is referred to as the flow area aspect ratio. The reported devices have had interstice aspect ratios of approximately 20 or lower and flow area aspect ratios of more than 5.

Actuator throw, or the amount of liquid that can be moved through the apparatus, is an important determinant of the types of applications for which an actuator can be used. An EO pump has been reported incorporating a solid structure consisting of arrays of holes in silicon [9]. This design was limited in actuator throw as a function of apparatus volume and maximum pressure.

Accordingly, conventional microfluidic actuators, including conventional EO microfluidic actuators, are limited in throw, response time, maximum pressure, and suitability for integration with other microfluidic components. The present invention addresses these and other shortcomings of the prior art.

SUMMARY OF THE INVENTION

An embodiment of the present invention comprises a device that includes a slat structure comprising a rigid structural frame supporting a plurality of approximately evenly spaced slats, wherein the slats have a thickness and wherein the slat structure comprises a plurality of interstices between the slats and the plurality of interstices comprises a plurality of fluid passageways extending through the thickness, such that a fluid is capable of flowing through the slat structure. Each of the interstices has a smaller in-plane cross-sectional dimension, or width, a and a larger in-plane cross-sectional dimension, or height, b, wherein a is between 1 and 10 microns and b is at least the lesser of fifty times greater than dimension a or 250 microns and the number of interstices is at least ten.

The device includes a housing enclosing the slat structure. The housing includes a first structure defining a first fluid cavity adapted for housing a fluid in fluidic communication on one side of the slat structure with fluid contained within the interstices. The housing also includes a second structure defining a second fluid cavity adapted for housing a fluid around the other side of the slat structure and maintaining said fluid in fluidic communication with fluid contained within the interstices. The first fluid cavity, the plurality of interstices, and the second fluid cavity define a fluid pathway, and a lowest flow resistance path from the first fluid cavity to the second fluid cavity is through the plurality of interstices.

The device has a plurality of electrodes for generating an electric field within the plurality of interstices.

In some embodiments, during operation, at least ⅔ of a maximum voltage difference $\Delta V$ applied across the plurality of electrodes occurs within the interstices. A component of the electric field is parallel to the direction of flow through the plurality of interstices.

In some embodiments, the slat structure is composed of an insulating material or a semi-conducting core material with surface coatings.

In another embodiment, an average electrical resistivity of the material composing the slat structure is at least 1000 ohm-centimeters.

In yet another embodiment, with an electrical potential difference applied across said electrodes, an electric field arises within some or all of the plurality of interstices, and wherein, in each of the plurality of interstices where an electric field arises, a component of the electric field is parallel to at least some of the walls of the interstice.

In some embodiments, dimension b is greater than or equal to 0.5 mm. In one embodiment, the sidewalls of the slats are straight. In another embodiment, the sidewalls of the slats are curved, saw-toothed, wavy, or otherwise non-rectilinear.

The thickness of the slats may be between 50 microns and 2 mm. In some embodiments, dimension a is 0.5 to 10 microns.

In some embodiments, the slat structure comprises silicon and is coated with one or more thin films. At least one of the thin film coatings may comprise silicon in combination other elements, such as oxygen and nitrogen. In one embodiment, the thin film comprises a nitrogen-containing silicon material. At least one coating may comprise a silicon oxide film. The slat structure may comprise a die cut from a crystalline silicon wafer. The silicon material may have a resistivity of at least 1000 ohm-centimeters.

In some embodiments, the plurality of interstices is approximately uniform in size and shape. In other embodiments, the plurality of interstices is approximately uniform in its smaller cross-sectional dimension a and non-uniform in its larger cross-sectional dimension b.

In another embodiment, the plurality of interstices collectively forms a flow passageway in which the in-plane dimensions of the area enclosing all interstices are within a factor of five of one another.

In other embodiments, the device also includes a volume of liquid wholly or partially filling said interstices and contacting the electrodes. In some embodiments, the liquid is an aqueous solution. In some embodiments, the liquid extends at least 100 microns into the first and second fluid cavities on either side of the slat structure.

In one embodiment, the plurality of electrodes is composed of stainless steel meshes with electroplated platinum.

In some embodiments, the device includes a battery or other electrical potential source. In some embodiments, the electrical potential source is coupled to a switching system, such that the voltage applied across the plurality of electrodes can be turned on and off. In some embodiments, the electrical potential can be turned on and off at a constant frequency and with a constant duty cycle, i.e. driven with a square wave input. The voltage pulse frequency may be 0.5 Hz or faster, 1.0 Hz or faster, 10 Hz or faster, or 100 Hz or faster. The ratio of time in the on state to time in the off state, or duty cycle, of the pulses may be any value between 0 and 100%.

In other embodiments, the device includes electronics such that the applied potential can be adjusted, either continuously or discretely, across a range of applied potentials.

In some embodiments, the composition of the surfaces of the sidewalls of the slats increase the density of mobile ions within the fluid phase of the electric double layer and to increase the volume of fluid within which the concentration of such mobile ions is sufficiently large to contribute to the generation of electroosmotic flow, such density and distribution effects for mobile ions being describable by an increase in the an absolute value of a zeta potential at an interface of the fluid and the slat surface material.

In other embodiments, the device also includes a signal generator and associated hardware for varying the electrical potential applied to the plurality of electrodes as a sine wave or arbitrary waveform.

In some embodiments, the device has a fluid power generation capacity of at least $10^8$ watts. In some embodiments, the device is capable of sustaining power for at least 30 seconds. In other embodiments, the device has a response time for power generation is less than 10 seconds.

In some embodiments, dimension a is approximately the same for each of the plurality of interstices.

The invention includes a method of manufacturing a fluidic device by generating a slat structure, wherein a separation between the first and second faces defines a thickness and wherein the plurality of interstices extending through the thickness are a fluid passageway from one side of the slat structure to the other side. The plurality of interstices has a smaller in-plane cross-sectional dimension, or width, a and a second in-plane cross-sectional dimension b, wherein dimension b is at least fifty times greater than dimension a, wherein dimension a is between 1 and 10 microns and dimension b is at least fifty times greater than dimension a, and wherein the average electrical resistivity of the slat material is at least 1000 ohm-centimeters.

The method includes generating a housing enclosing the slat structure that includes a first structure defining a first fluid cavity adapted for housing a fluid and in fluidic communication with the plurality of interstices. The method also includes generating a housing enclosing the slat structure that includes a second structure defining a second fluid cavity adapted for housing a fluid and in fluidic communication with the plurality of interstices. The first fluid cavity, the plurality of interstices, and the second fluid cavity define a fluid pathway. In some embodiments, a lowest flow resistance path from the first fluid cavity to the second fluid cavity is through the plurality of interstices.

The method includes providing a plurality of electrodes for generating an electric field within the plurality of interstices of said slat structure, wherein the slat structure, the housing and the plurality of electrodes are configured such that, during operation, at least ⅔ of a maximum voltage difference ΔV applied to the plurality of electrodes occurs within the interstices.

The method can include adding a conformal insulating layer to at least one surface of the slat structure to minimize electrical charge transfer between the fluid and the slat structure. The method also can include adding a conformal insulating layer to at least one surface of the slat structure to maximize an absolute value of a zeta potential at an interface of the fluid and the slat structure. In some embodiments, the electric field has a component parallel to the walls of said interstices.

The method also includes coating the slat structure with one or more thin films of silicon. In some embodiments, the thin film comprises silicon oxide. In other embodiments, the method includes coating the slat structure with one or more thin films of silicon nitride. In some embodiments, the slat structure comprises crystalline silicon. The crystalline silicon wafer may have a resistivity of at least 1000 ohm-centimeters.

In some embodiments, the plurality of interstices is produced by photolithographically patterning a plurality of slat structures on a crystalline silicon wafer, etching the plurality of interstices through bombardment with directional ions, removing a photolithography process residue and dicing said wafer into individual slat structures. The method also can include thinning the wafer prior to dicing by means of a chemical-mechanical polishing process. The method also can include providing a volume of aqueous solution in the housing, such that the volume extends at least 100 microns into the first and second fluid cavities on either side of the slat structure.

The method also can include connecting a battery or other electrical potential source to the plurality of electrodes. The method can also include connecting an electrical switching apparatus to the voltage source. The switch can be a programmed pulse generator to deliver a pattern of voltage pulses to the plurality of electrodes. The pattern of voltage pulses may repeat at a frequency of 0.5 Hz or faster, a frequency of 1.0 Hz or faster or a frequency of 10 Hz or faster. The pattern of voltage pulses may repeat at a frequency of 100 Hz or faster. In some embodiments, the fluid power output is controlled by the duty cycle of the pulses.

In one embodiment, the duty cycle is between 1 and 90%. In some embodiments, the pulse duration is shorter than a period of time corresponding to a 1/pattern repeat frequency.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 11 illustrates flow rate and power data for microfluidic actuators as summarized in FIG. 7, according to one embodiment of the invention.

DETAILED DESCRIPTION OF THE INVENTION

Electroosmosis is an electrochemical effect in which a fluid phase moves relative to a stationary solid phase. This movement of the fluid phase is associated with the interaction of an imposed electrical field and the mobile ions in the fluid phase of the electrical double layer that forms at many fluid-solid interfaces.

Figure 1:
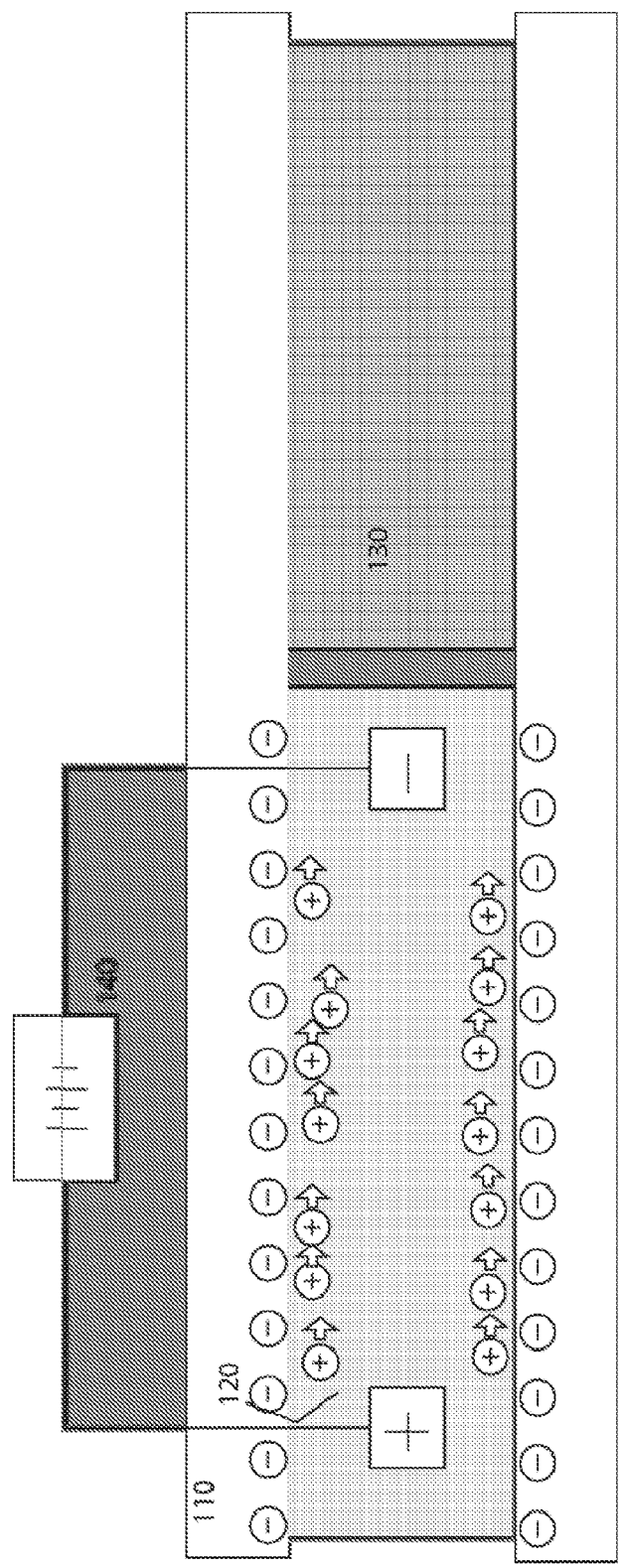
FIG. 1 illustrates the principle of using electroosmotic flow as the basis of a microfluidic actuator, according to an embodiment of the invention.

FIG. 1 illustrates the principle of electroosmotic flow. At the interface between a fluid phase and a solid phase, chemical reactions between the two phases typically result in the formation of a charge double layer, with a net charge at the surface of the solid and net charge of the opposite polarity in the fluid phase. For example, at the interface between an oxygen-containing silicon material 110, such as glass or silica, and a neutral-to-basic aqueous fluid phase, surface silanol groups tend to donate protons to form hydronium ions in the fluid phase, leaving a negative surface charge. An electrical double layer 120 forms as a result. The double layer 120 refers to two parallel layers of charge at the surface, where the first layer comprises ions adsorbed directly onto the object and the second layer composed of ions attracted to the surface charge via a coulomb force, electrically screening the first layer. The second layer is loosely associated with the surface because it is made up of free ions, which are attracted to the surface from within aqueous solution. The surface charge attracts dissolved counter-ions and repels co-ions, resulting in a charge separation. The Debye length is the characteristic thickness of the double layer 120. The term electrokinetic effects is used to describe phenomena associated with the electric double layer [10].

Electroosmotic flow is a term for bulk fluid flow associated with the body forces on the mobile ions in the diffuse counter-ion layer caused by an externally applied electrical field, and the moving ions drag along bulk liquid through viscous effects. FIG. 1 also shows the direction of electroosmotic flow from low pressure to high pressure, which is in opposition to the direction of the pressure driven flow.

In an electroosmotic actuator, fluid power associated with electroosmostic flow can do mechanical work on a mass 130 external to the apparatus within which electroosmotic flow is generated.

Burgeen and Nakache [11] developed a mathematical model which gives the average velocity of electroosmotic flow between two parallel surfaces sufficiently wide and long that flow is approximately one-dimensional. With the flow parallel to the coordinate axis x, for. an axial electric field $E_x$, permittivity $\varepsilon$, fluid viscosity $\mu$, and is:

$$\bar{v} = -\frac{a^2}{3\mu}\frac{dp}{dx} - \frac{\varepsilon\zeta}{\mu}E_x[1 - G(\alpha, \kappa a)]$$

where a is one-half the separation distance between the two parallel surfaces, $\mu$ is the fluid viscosity, $dp/dx$ is the pressure gradient counter to the flow, $\varepsilon$ is the fluid permittivity, $\zeta$ is the zeta potential, $\alpha$ is an ionic energy parameter, and G is a correction term for the thickness of the double layer. Applying an axial electric field exerts forces on the mobile ions, and electromigration of the mobile ions results in bulk fluid flow through viscous effects. The zeta potential is an empirical parameter characterizing the effect of the surface condition on the electroosmotic flow. The zeta potential is determined from the net excess of surface charge-balancing ions near the surface/fluid interface.

Definitions

Terms used in the claims and specification are defined as set forth below unless otherwise specified.

"Electroosmotic flow" refers to the movement of liquid induced by an applied potential across a fluid conduit. The fluid conduit can be any porous material, capillary tube, membrane, substrate, microchannel or passageway for allowing the flow of liquid. The electric potential can be applied between any two parallel surfaces.

A "microfluidic actuator" refers to a component that converts electrical power or another readily stored or generated form of energy into fluid power, and which can do mechanical work on a mass external to the electroosmotic flow region within the.

"Maximum back pressure" is the lowest back pressure at which, for a given working fluid, applied potential, and other parameters, the flow rate Q is zero or negative. For a microfluidic actuator's pressure-curve plotted with the flow rate on the x-axis and the back pressure on the y-axis, the maximum back pressure is the y-intercept of the pressure-flow rate curve.

A "slat" refers to a narrow strip of material. The slats may be composed of an insulating material or a semi-conducting core material with surface coatings.

It must be noted that, as used in the specification and the appended claims, the singular forms "a," "an" and "the" include plural references unless the context clearly dictates otherwise.

Overview

The microfluidic device is an apparatus for transducing electrical power into fluid power by means of electroosmosis.

Figure 2:
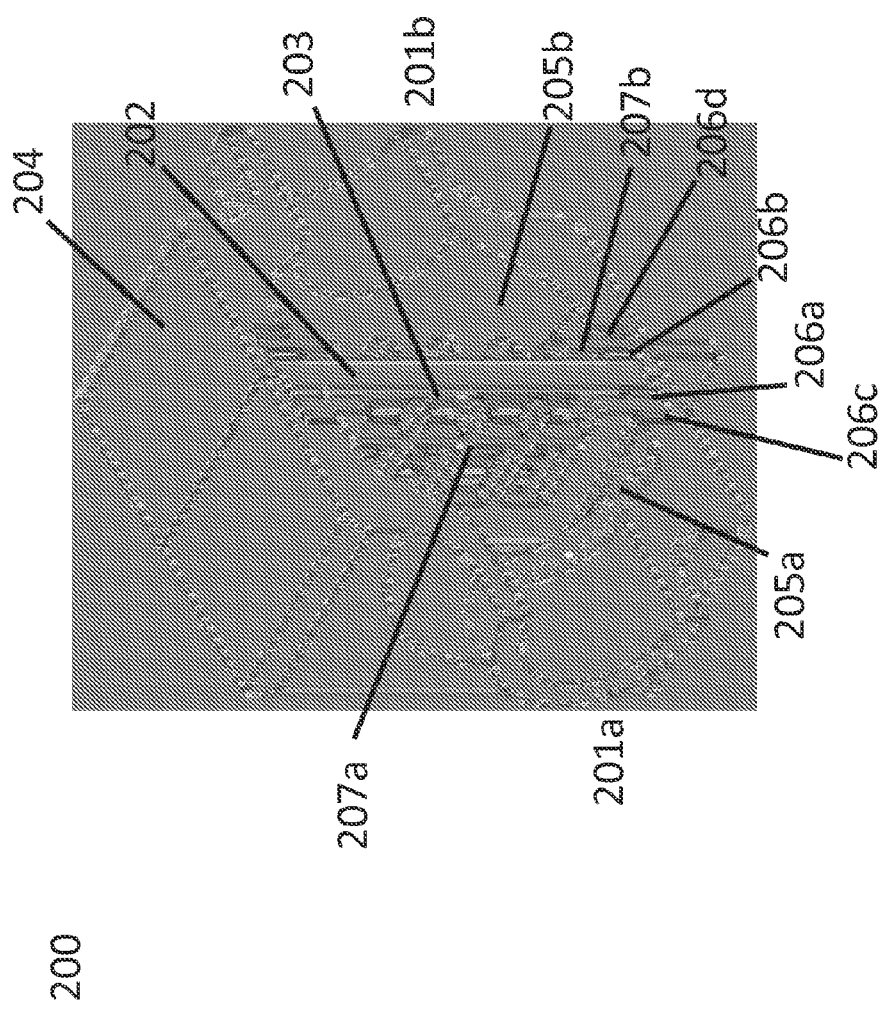
FIG. 2 is an example of a microfluidic actuator shown in isometric section perspective view, according to an embodiment of the invention.

FIG. 2 shows, in a section isometric perspective view, an example of the microfluidic device 200, according to one embodiment of the invention. The device 200 comprises ports 201a, 201b for receiving fluids and for acting on external masses. Fluid may enter and exit from outside the device 200 via the openings 201a, 201b. There may be fluid passageways that are connected to the device 200 via the openings 201a, 201b, and the fluid passageways may be filled with fluid.

The device 200 comprises a plurality of slats forming a three-dimensional structure 202, each slat having a first face and a second face and a first sidewall and a second sidewall. The slat structure 202 may also be called an EO flow structure or a slit capillary array (SCA). The separation between the first and second faces of the slats defines a thickness. The slat structure includes a plurality of interstices 203 extending through the slat structure. The plurality of interstices 203 are passageways through which fluid can pass from one side of the slat structure to the other. There may be 10, 15, 20, 25, 30, 35, 40, 45, 50, or more slats, with a corresponding number of interstices. As shown in FIG. 2, the interstices 203 may be approximately uniform in shape. The interstices 203 may also be called slits or slit capillaries. In other embodiments, the slats 202 are wedge-shaped instead of rectangular, and the interstices 203 are arranged radially instead of in rows. In some embodiments, the interstices 203 have straight sides. In other embodiments, the interstices have wavy, curved, or saw-toothed sides. The interstices 202 may be non-uniform in size and shape, although the smaller of the two cross-sectional dimensions will generally be approximately uniform among all the interstices in a particular microfluidic actuator. The slats that comprise the slat structure 202 may be non-uniform in size and shape. In some embodiments, the slats 202 are arranged in a M×N array, where there are M rows and N columns of interstices.

Each interstice 203 has three major dimensions: an in-plane dimension a, a second in-plane dimension b, and a third dimension/that runs the length of the thickness. In some embodiments, the in-plane dimension a is uniform for all of the interstices 203. In other embodiments, the in-plane dimension a is approximately the same for the interstices 203. In another embodiment, dimension a is 1 to 10 microns. In one embodiment, the second in-plane dimension b is twenty, fifty, or hundred times greater than the in-plane dimension a. In another embodiment, dimension b is greater than or equal to 0.5 mm. In yet another embodiment, the thickness dimension/(slat thickness) is between 50 microns and 2 mm in length. The collection of interstices has two major dimensions: a first in-plane dimension F and a second in-plane dimension G, which is also described in FIG. 5. In some embodiments, the ratio of F to G is between 0.2 and 5.

Whereas the nominal model of electroosmotic flow between two wide parallel slat structures indicates that maximum back pressure is independent of b and maximum flow rate is proportionate to b, it has been experimentally observed that, for b greater than approximately 20, increasing b is associated with increasing and increases in $Q_{max}$ greater than those. This effect is seen in EO devices with flow area aspect ratio of less than five.

The slat structure 202 may be assembled from individual slats or produced as a perforated sheet or a perforated block of solid material. In other embodiments, the slat structure 202 is composed of borosilicate glass or silicon. In some embodiments, the slat structure 202 comprises silicon with electrical resistance of at least 1000 ohm-centimeters. In other embodiments, the slat structure is coated with one or more silicon-containing thin films. In other embodiments, the slat structure may be coated with one or more thin films of silicon oxide. In other embodiments, the slat structure 202 may be coated with one or more thin films of silicon nitride. In other embodiments, the slat structure 202 may comprise crystalline silicon. In yet other embodiments, the slat structure 202 is a single-crystal silicon coated with multiple layers of silicon oxide and silicon nitride. In other embodiments, the slat structure is a molded thermoplastic.

In yet other embodiments, the device 200 includes a conformal insulating layer on at least one of the first and the second faces of the slat structure 202. The insulating layer is capable of reducing the occurrence of an electrochemical reaction between the fluid and the slat structure 202. In other embodiments, the insulating layer is capable of increasing an absolute value of a zeta potential at an interface of the fluid and the slat structure 202.

In an embodiment, the interstices 203 in the slat structure 202 are made by a photolithographic feature definition process followed by time-multiplexed inductively coupled plasma (TM-ICP) etching, also known as deep-reactive ion enhanced (DRIE) etching [12].

The microfluidic device 200 also includes a housing 204 enclosing the slat structure 202. The housing 204 has a first structure that defines a first fluid cavity 205a adapted for housing a fluid and in fluidic communication with the either the first face or the second face of the slat structure. The housing 204 has a second structure defining a second fluid cavity 205b adapted for receiving the fluid and in fluidic communication with the other face of the slat structure. The first fluid cavity 205a, the plurality of interstices 203, and the second fluid cavity 205b define a fluid pathway, wherein a lowest flow resistance path from the first fluid cavity 205a to the second fluid cavity 205b is through the plurality of interstices 203 in the slat structure 202.

The first and second structures may be sealed around the periphery, such that the only path for fluid from one cavity to the other is through the plurality of interstices 203 in the slat structure 202. The first and second structures can be in fluid communication with external passageways by means of the openings 201a and 201b through which fluid may enter and exit from outside the housing. The fluid passageways that are connected to the housing may be filled with fluid.

In some embodiments, the microfluidic device 200 includes a plurality of gaskets 206a, 206b which seal around the slat array.

The microfluidic device 200 includes a plurality of electrodes 207a, 207b for generating electric fields within the plurality of interstices 203. In some embodiments, a plurality of gaskets seal 206c, 206d around the plurality of electrodes 207a, 207b. In some embodiments, the slat structure 202, plurality of interstices 203, housing 204 and electrodes 207a, 207b are configured such that when the fluid cavities 205a and 205b and the interstices are wholly filled with a fluid which is substantially spatially uniform in charge density. In other terms, the slat structure 202, plurality of interstices 203, housing 204 and electrodes 207a, 207b are configured such that when the fluid cavities 205a and 205b and the interstices are filled with an aqueous solution and chemical or electrochemical reactions between said aqueous and the electrodes 207a, 207b maintain spatially uniform charge density for a voltage difference ΔV applied across the plurality of electrodes 207a, 207b, such that the average axial electrical field within each interstice is 0.667 ΔV/l. In some embodiments, the distance between each electrode and the corresponding face of the slat structure is less than 1 millimeter.

In some embodiments, the electrodes 207a, 207b are stainless steel meshes with electroplated platinum. In some embodiments, the electrodes 207a, 207b are drawn platinum wire electrodes. In other embodiments, the electrodes 207a, 207b are silver or silver chloride electrodes and are printed on a surface within a cavity or on the slat structure 202 itself.

Figure 3:
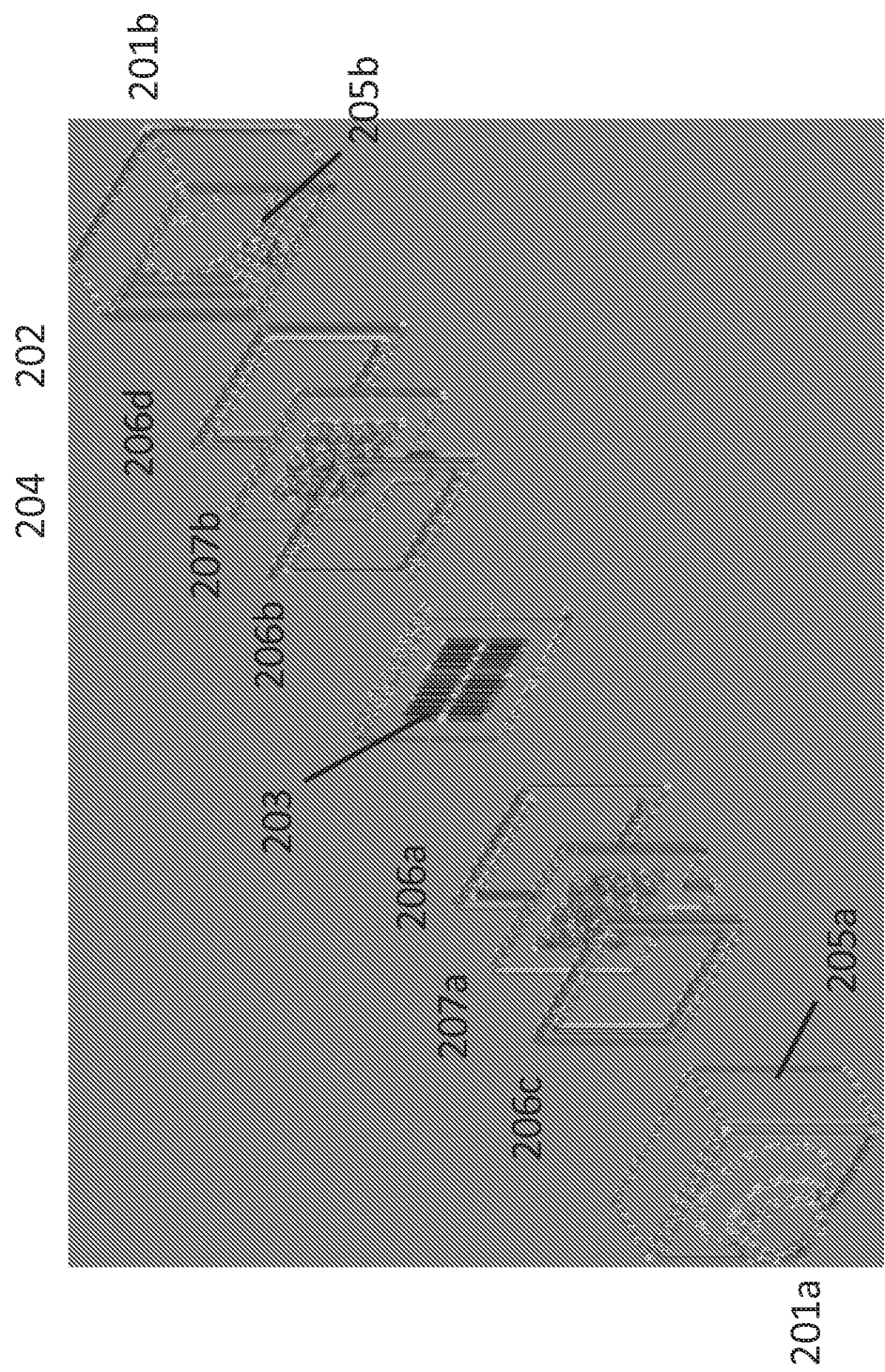
FIG. 3 is an example of a microfluidic actuator shown in isometric exploded view, according to an embodiment of the invention.

FIG. 3 is an exploded view of a microfluidic device 200, according to one embodiment of the invention, with components as described above in FIG. 2.

Figure 4:
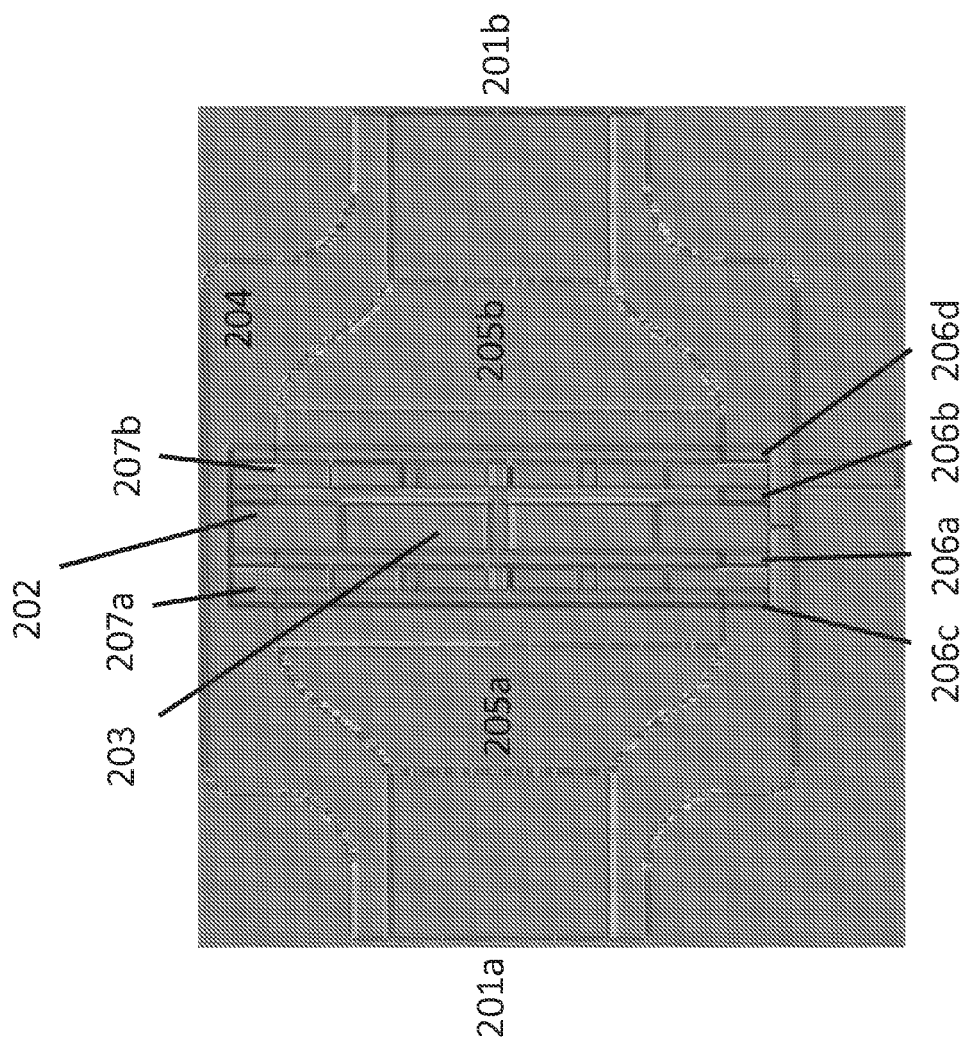
FIG. 4 is a side view of a microfluidic actuator, according to an embodiment of the invention.

FIG. 4 is a side section view of the device 200, according to one embodiment of the invention, with components as described above in FIG. 2.

Figure 5:
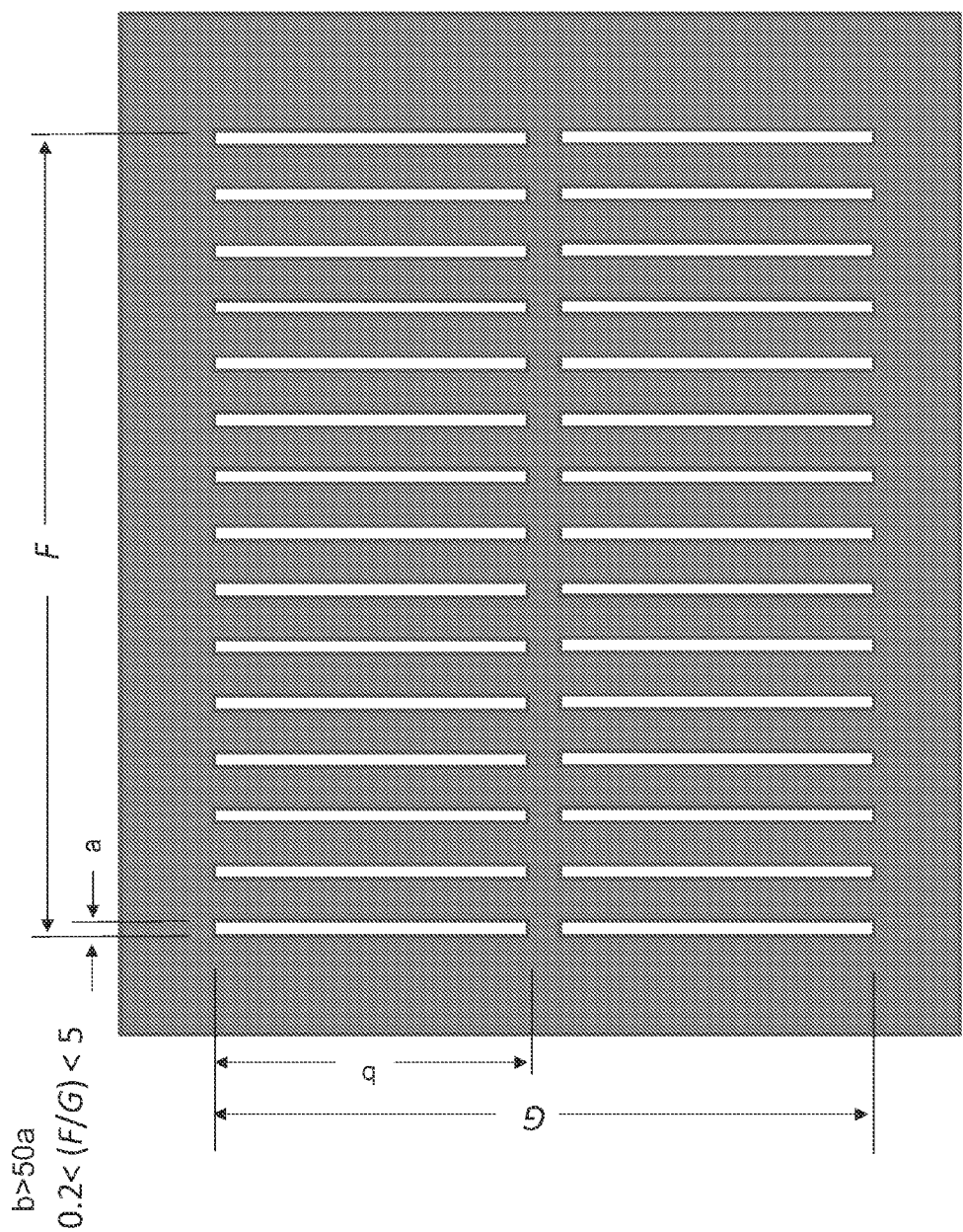
FIG. 5 illustrates an array of interstices on a microfluidic actuator, according to an embodiment of the invention.

FIG. 5 illustrates the dimensions of the interstices 203, individually and collectively, in the slat structure 202, according to one embodiment of the invention. The first in-plane dimension a and the second in-plane dimension b are shown from an angle facing one of the faces of the slat structure 202. Here, dimension b is shown to be at least 50 times greater than dimension a. The in-plane dimension a can also be characterized by its half-length ½ a (where a=½ a). Collectively, the plurality of interstices forms a fluid passageway with external dimensions F and G, where the ratio of F to G is between 0.2 and 5.

In other embodiments, the device 200 may be coupled to a pulse generator programmed to deliver a pattern of voltage pulses to the plurality of electrodes 207a, 207b. The pattern of voltage pulses may repeat at a frequency of 0.5 Hz or faster, at a frequency of 1.0 Hz or faster, at a frequency of 10 Hz or faster, or at a frequency of 100 Hz or faster. In some embodiments, the pattern of voltage pulses is a pulse duration. The pulse duration may be shorter than a period of time corresponding to a 1/pattern repeat frequency. The ratio of time in the on state to time in the off state, or duty cycle, of the pulses may be any value between 0 and 100%.

In some embodiments, the device 200 has a fluid power generation capacity of at least $10^8$ watts. In some embodiments, the device 200 is capable of sustaining power for at least 30 seconds. In other embodiments, the device 200 has a response time for power generation is less than 10 seconds.

Figure 6:
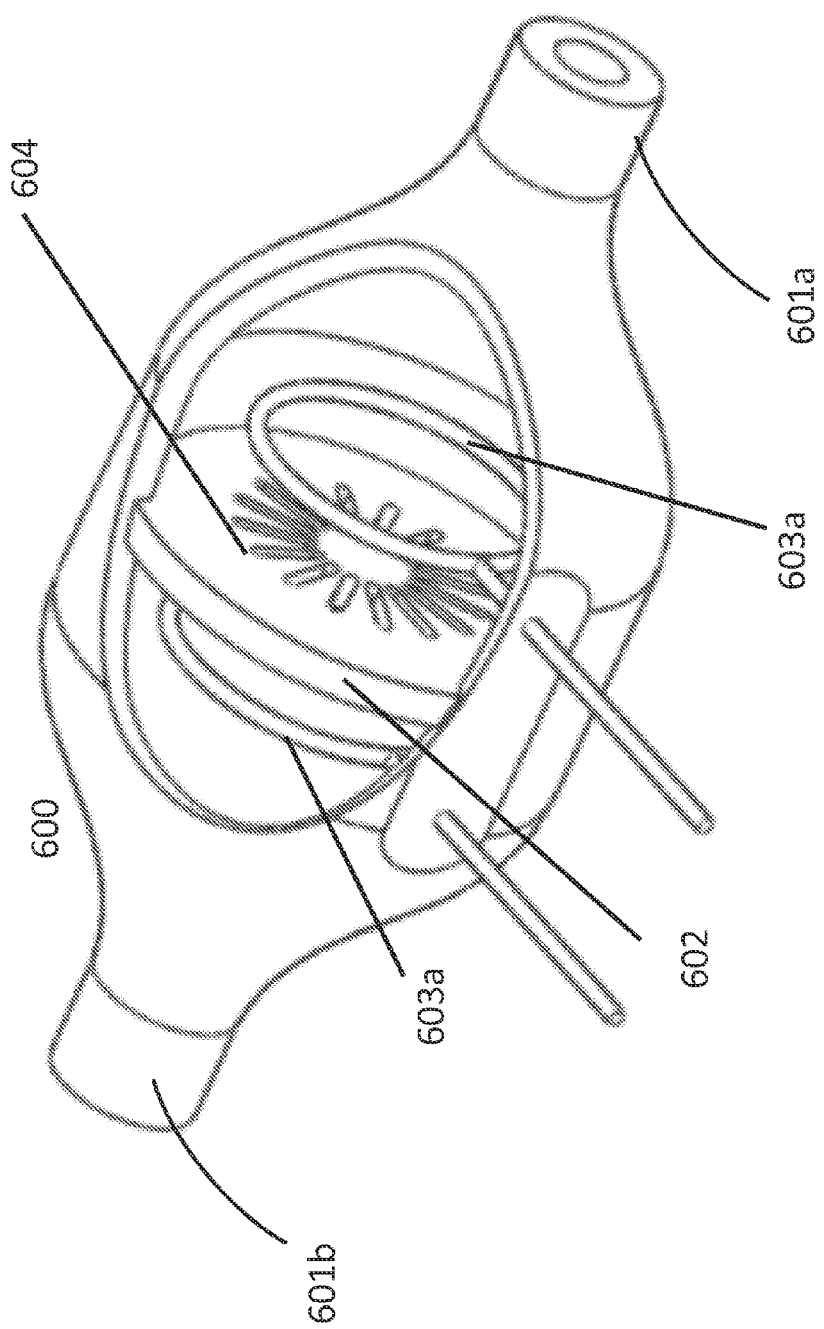
FIG. 6 is an example of a microfluidic actuator, according to an embodiment of the invention.

FIG. 6 shows an embodiment of a microfluidic device 600, where the configuration of interstices 604 are positioned in an axial array in the slat structure 602. The electrodes 603a are positioned on either side of the slat structure 602. The microfluidic device 600 includes openings 601a and 601b.

The following calculations are used to demonstrate the fluidic capacity of the microfluidic device 200.

In another embodiment, the total flow cross-sectional area ($A_{SCA}$) through the interstices of the slat structure 202 is calculated by the following:

$$A_{SCA} = A_{TOT} = n_1 AB \quad \text{(Equation 1)}$$

where the interstices in the slat structure 202 are arranged in a M×N array, having M interstices in one in-plane dimension, and N interstices in the second in-plane dimension, and where half-length of the in-plate dimension of the interstice is a and the second in-plate dimension is b.

The average flow velocity can also be calculated for the microfluidic device 200. It has been shown that a spatially and temporally constant axial electric field $E_x$ within a slit capillary produces electroosmotic flow with an average axial flow velocity U of:

$$U = -\frac{a_s^2}{3\mu l_s}\Delta p_s + \frac{\varepsilon \zeta}{\mu} E_x [1 - G(\alpha, \kappa a_s)] \quad \text{(Equation 2)}$$

See R. J. Hunter, *Zeta Potential in Colloid Science*. San Diego: Academic Press, Inc., 1981; D. Burgreen and F. R. Nakache, "Electrokinetic Flow in Ultrafine Capillary Slits," *J. Phys. Chemistry*, vol. 68, pp. 1084-1091, 1964.

The slit capillary end-to-end differential pressure $\Delta p_s$ may be externally imposed and/or arise as a consequence of an external load in series with the slit capillary. For the prescribed values of $a_s < 5$ μm, the thin electric double layer (EDL) assumption is almost always appropriate for the slat structure 202 within the device 200, regardless of the choice of working fluid.

Furthermore, the flow rate-pressure can be calculated for the microfluidic device 200. The flow rate-pressure relationship is as follows:

$$Q = A_{SCA}\left[-\frac{a_s^2}{3\mu l_s}\Delta p_{SCA} - \frac{\varepsilon \zeta}{\mu l_s} V_s\right] \quad \text{(Equation 3)}$$

Previously designed actuators have been designed with an array of openings having dimensions 2 μm≤a≤4 μm, 50 μm≤b≤200 μm, 100 μm≤l≤500 μm arranged in a one-dimensional M×N array (200≤N≤1000, M=1). These actuators operate at between 100 and 500 volts with a working fluid of deionized water or a similar aqueous solution, generate maximum flow rates on the order of 100 microliters per minute and maximum back pressures on the order of 1 kPa.

For the microfluidic device 200 of the invention, both $\Delta P_{max}$ and $Q_{max}$ increase by approximately an order of magnitude. According to Equation 3, $Q_{max}$ is expected to scale with $A_{SCA}$, which in turn increases with increasing m. The increase in $\Delta P_{max}$ demonstrated by the microfluidic device 200 of the invention, however, is not predicted by Equation 4. The spatially complex fluid dynamic effects, electric field effects, or a combination of the two causes the more efficient generation of fluid power in an actuator with M>1.

Figure 7:
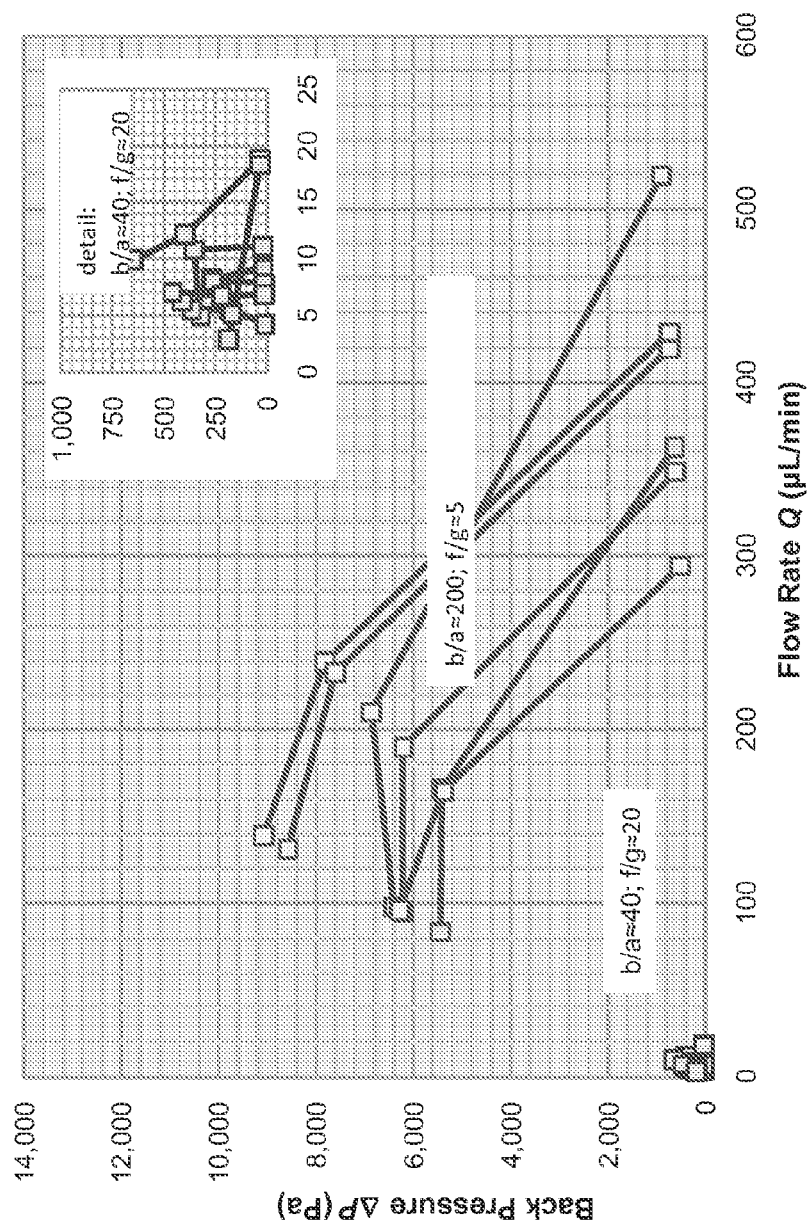
FIG. 7 illustrates the back pressure and flow rate performance among microfluidic actuators according to one embodiment of the invention with comparison to performance of microfluidic actuators described in the prior art.

FIG. 7 shows a comparison of a microfluidic device 200 of the present invention and a "first-generation" actuator. The plotted curves show the relationship between back pressure ΔP (the pressure associated with fluidic resistance in the system within which the microfluidic actuator operates) as a function of the flow rate Q through the actuator. First-generation actuators typically produce maximum flow rates $Q_{max}$ (reagent transport against negligible back pressure) of 10-50 microliters per minute, with maximum back pressure $\Delta P_{max}$ (back pressure at which Q approaches zero) of 200-1000 pascals. The microfluidic actuator 202 of the present invention has a $Q_{max}$ of 300-800 microliters per minute and $\Delta P_{max}$ of 5-10 kPa. The increase in Qmax is consistent with the greater flow cross-sectional area of the actuator. FIG. 7 illustrates the increased flow rate and back pressure capacity of the microfluidic device 200 of the invention ($\Delta P_{max}$ and $Q_{max}$), compared with first-generation microfluidic actuators.

Figure 8:
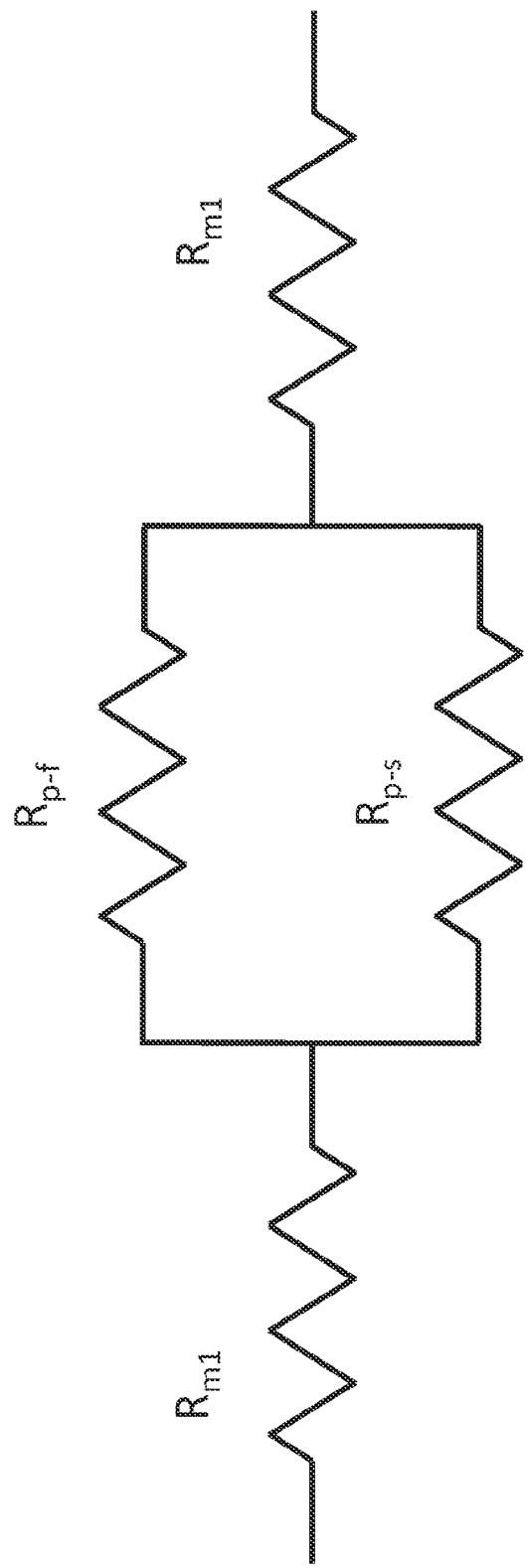
FIG. 8 illustrates the electrical resistance across the actuator in the microfluidic device, according to one embodiment of the invention.
Figure 9:
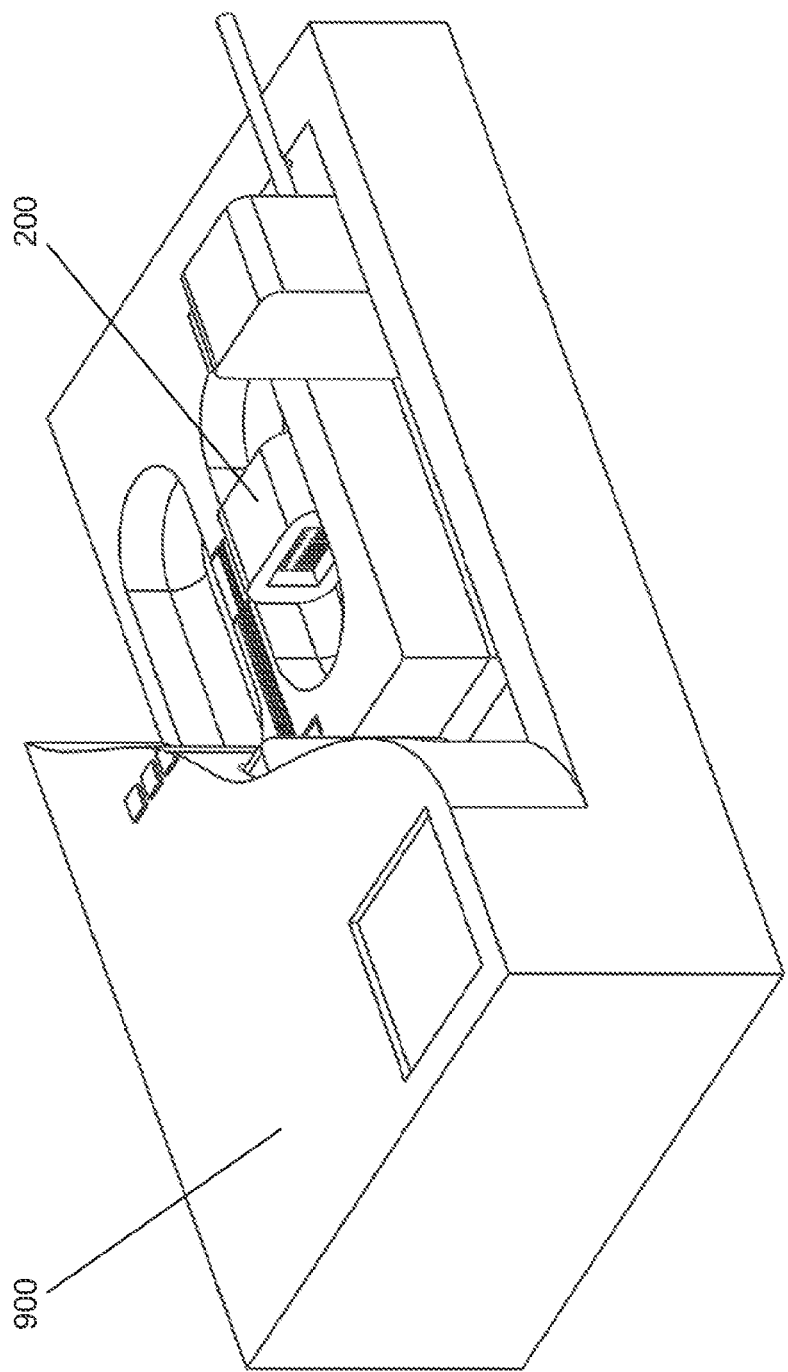
FIG. 9 is an example of a microfluidic cartridge comprising one or more microfluidic actuators of the invention, according to one embodiment of the invention.

FIG. 8 provides an illustration of the electrical resistance across the slat structure 202. FIG. 9 illustrates a microfluidic cartridge or processing system 900 that houses the microfluidic actuator 200. One or more microfluidic actuators 200 may be used in the microfluidic cartridge 900.

EXAMPLES

Below are examples of specific embodiments of the invention. The examples are offered for illustrative purposes only, and are not intended to limit the scope of the present invention in any way.

Example 1: Method of Generating a Microfluidic Device

Methods of the invention include methods of manufacturing a microfluidic device. The method includes generating a slat structure, each slat having a first face and a second face, wherein a separation between the first and second faces defines a thickness and wherein the slat structure comprises a plurality of interstices such that a fluid is capable of flowing through the plurality of interstices. Each of the plurality of interstices has a dimension a across the face of the interstice and a dimension b of the length of the thickness, wherein the dimension b is between 50 microns and 2 mm in length, and is at least fifty times greater than dimension a of the interstice, and wherein the average electrical resistivity of the primary structural material composing the slat structure is at least 1000 ohm-centimeters.

In one embodiment, the method includes generating a housing enclosing the slat structure, such housing including a first housing structure and a second housing structure. The first housing structure defines a first fluid cavity adapted for housing a fluid and in fluidic communication with one face of the slat structure. The second housing structure defines a second fluid cavity adapted for housing a fluid and in fluidic communication with the other face of the slat structure. In some embodiments, the first fluid cavity, the slat structure and the second fluid cavity define a fluid pathway, wherein the lowest flow resistance path from the first fluid cavity to the second fluid cavity is through the plurality of interstices.

The method also includes providing a plurality of electrodes for generating an electric field within the plurality of interstices. In some embodiments, the slat structure, the housing and the electrodes are configured such that at least ⅔ of a maximum voltage difference ΔV applied to the plurality of electrodes occurs between the first face and the second face of the slat structure. In some embodiments, the electric field is perpendicular to the surface of the slat structure.

The method includes adding a conformal insulating layer to at least one surface of the slat structure, or to the individual slats, to minimize electrical charge transfer between the fluid and the slat structure. The method also includes adding a conformal insulating layer to at least one surface of the slat structure to increase the density of mobile ions within the fluid phase of the electric double layer and to increase the volume of fluid within which the concentration of such mobile ions is sufficiently large to contribute to the generation of electroosmotic flow, such density and distribution effects for mobile ions being describable by an increase in an absolute value of a zeta potential for the interface of a fluid phase and the slat structure surface material. The method also includes coating the slat structure with one or more thin films of silicon. In some embodiments, the thin film comprises silicon oxide. In other embodiments, the method includes coating the slat structure with one or more thin films of silicon nitride. In one embodiment, the slat structure comprises crystalline silicon. The crystalline silicon may have a resistivity of at least 1000 ohm-centimeters.

In other embodiments, the slats have straight sides. In another embodiment, the sides of the slats are wavy, curved, saw-toothed, or are otherwise non-rectilinear shape.

In some embodiments, the slat structure is produced by photolithographically patterning a single-crystal silicon wafer, etching a plurality of interstices through bombardment with directional ions, removing a photolithography process residue, producing at least one surface film through deposition or other means, and dicing the wafer. In some embodiments, the method also includes thinning the wafer by means of a chemical-mechanical polishing process. In some embodiments, the method includes oxidizing the etched silicon wafer after etching such that the slats are enlarged through the conversion of silicon to silicon oxide, with a corresponding reduction in the interstice width. In some embodiments, the method includes depositing polysilicon on the wafer after etching such that the slats are enlarged, with a corresponding reduction in the interstice width.

The method also includes providing a volume of aqueous solution in the housing, such that the volume extends at least 100 microns into the first and second fluid cavities on either side of the slat structure.

The method also includes programming a pulse generator to deliver a pattern of voltage pulses to the plurality of electrodes. The pattern of voltage pulses may repeat at a frequency of 0.5 Hz or faster, a frequency of 1.0 Hz or faster, or a frequency of 10 Hz or faster. The pattern of voltage pulses repeats at a frequency of 100 Hz or faster. In some embodiments, the pattern of voltage pulses is a pulse duration. In one embodiment, the pulse duration is shorter than a period of time corresponding to a 1/pattern repeat frequency.

Example 2: Microfluidic Cartridge

The microfluidic device 200 may be housed in a microfluidic cartridge 900, as shown in FIG. 9. In some embodiments, at least two microfluidic devices or actuators are included in the microfluidic cartridge 900. The microfluidic cartridge may also include a plurality of fluid passageways that are fluidly connected to the microfluidic device, openings for receiving fluids, and components for processing, mixing and analyzing fluids.

Alternating plugs of fluids can be generated from the use of two or more microfluidic devices (or actuators) pressurizing two or more fluids inside the microfluidic cartridge 900. In an example, operating a first microfluidic actuator 200 or a second microfluidic actuator, or both, in a time-varying manner can result in spatially non-uniform distributions of the fluids for the series of cross-sections in the axial direction within the fluid passageway. The first microfluidic actuator 200 can be toggled between an on-state and an off-state with a duty cycle of 50%, and the second microfluidic actuator can be toggled between an on-state and an off-state with a duty cycle of 50%, such that the microfluidic actuators operate 180 degrees out of phase from one another.

Figure 10:
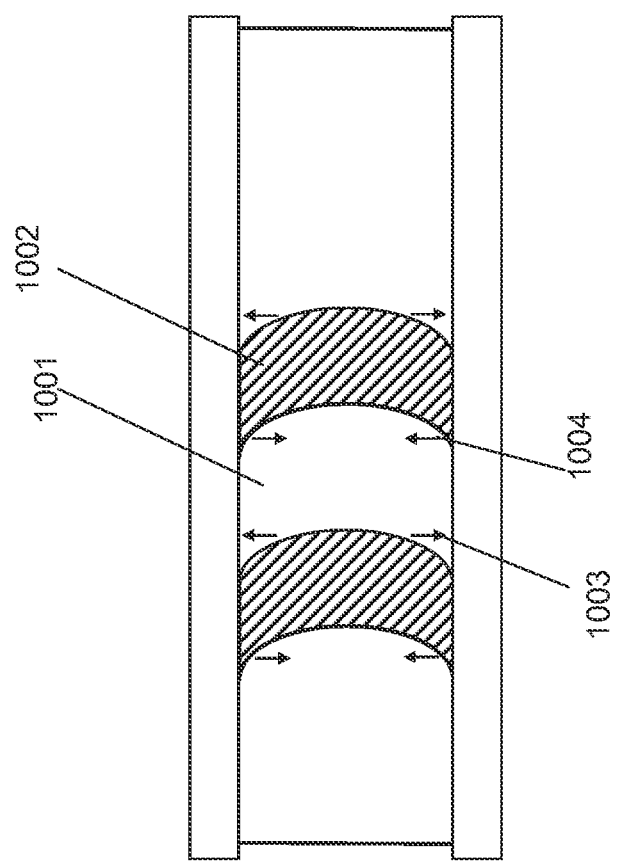
FIG. 10 illustrates an example of alternating plugs of fluids in a fluid passageway, according to one embodiment of the invention.

FIG. 10 shows a sequential injection of alternating plugs 1001, 1002 of fluids contained in the fluid passageways. Because of predominance of viscous forces over inertial forces, molecular diffusion can be the primary mechanism by which chemical and biochemical constituents of two fluids intermingle when such fluids are combined within a microfluidic cartridge. Spatially non-uniform distributions of fluids can shorten the distances over which such diffusion takes place, speeding chemical and biochemical reactions. For greater control over differential fluid transport and/or to mix multiple fluids together, multiple microfluidic actuators may be used with multiple channels and junctions for moving and combining fluids. Each microfluidic actuator is fluidly connected to an actuator fluid and generates flow of a processing fluid. For example, two microfluidic actuators can generate mixing of two processing fluids. Next, the mixture can be joined with a third fluid in another fluidic passageway using the fluidic pressure of two additional microfluidic actuators.

FIG. 10 illustrates a sequential injection of alternating plugs of the fluids followed by pressure-driven flow of the train of plugs through a fluid passageway. Fluid flows in the low Reynolds number regime can be well modeled by assuming the flow velocity at the fluid passageway wall to be zero (the no-slip boundary condition). For a cylindrical passageway, the radial flow velocity profile is parabolic:

$$u(r) = 2U\left[1 - \left(\frac{r}{a}\right)^2\right]$$

where U is the average velocity, r is the radial coordinate, and a is the radius of the cylindrical passageway. As the plugs move down the fluid passageway, the parabolic flow profile causes corresponding plug distortion 1001, 1002. Any particles or molecules contained with the fluid plugs can diffuse radially from the distorted plugs. For example, the particles or molecules can diffuse radially outward 1003 from the plug fronts near the fluid passageway centerline and radially inward 1004 from the plug tails near the walls. This phenomenon is known as Taylor dispersion. Similar diffusion effects can arise in non-cylindrical fluid passageways.

Taylor dispersion between alternating plugs of fluid generated by the microfluidic actuator 200 may be used to mix reagents or molecules within two different fluids. For example, the mixing of fluids may be used to label analytes or molecules or bind target molecules with antibodies or molecular probes.

FIG. 11 further provides flow rate and power data for microfluidic actuators as summarized in FIG. 7, according to one embodiment of the invention.

Figure 12:
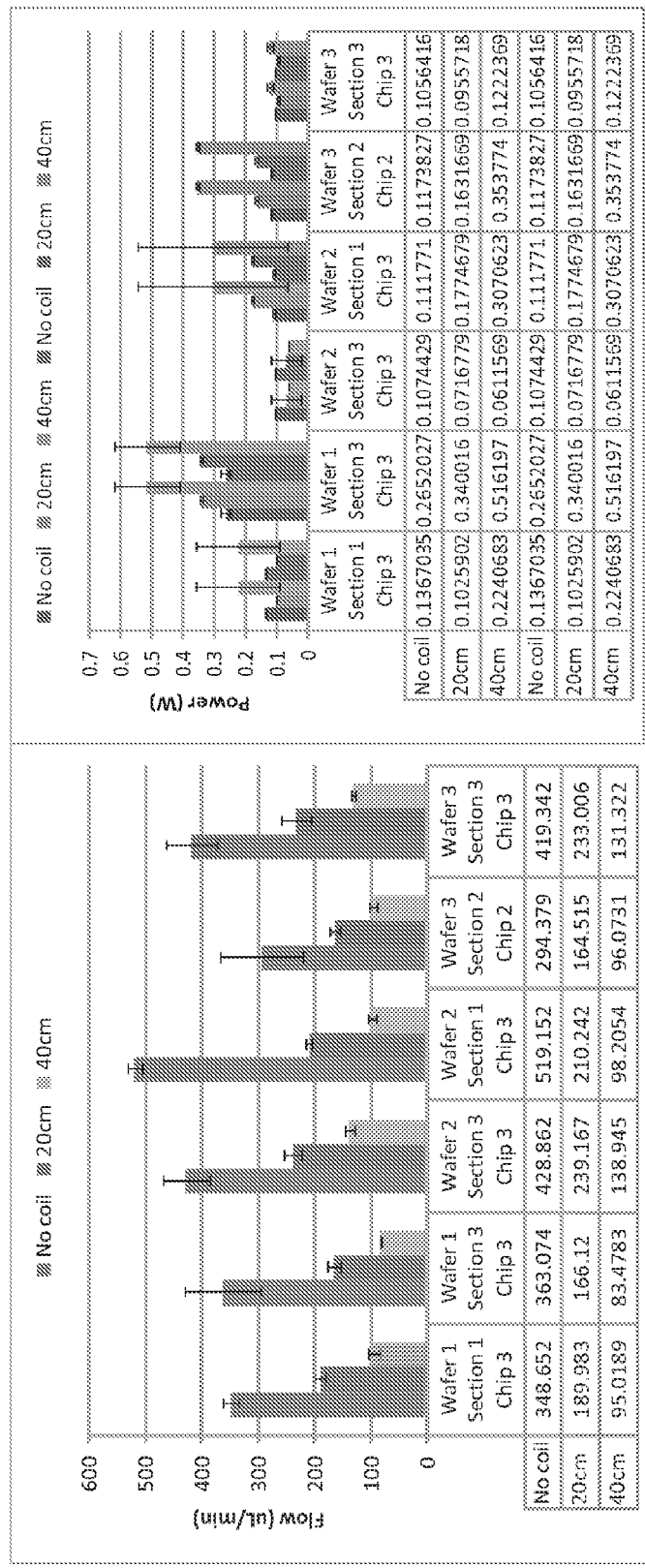
FIG. 12 illustrates graphs of the flow rate and power data for microfluidic actuators as summarized in FIGS. 7 and 11, according to one embodiment of the invention.

FIG. 12 illustrates graphs of the flow rate and power data for microfluidic actuators as summarized in FIGS. 7 and 11, according to one embodiment of the invention.

Figure 13:
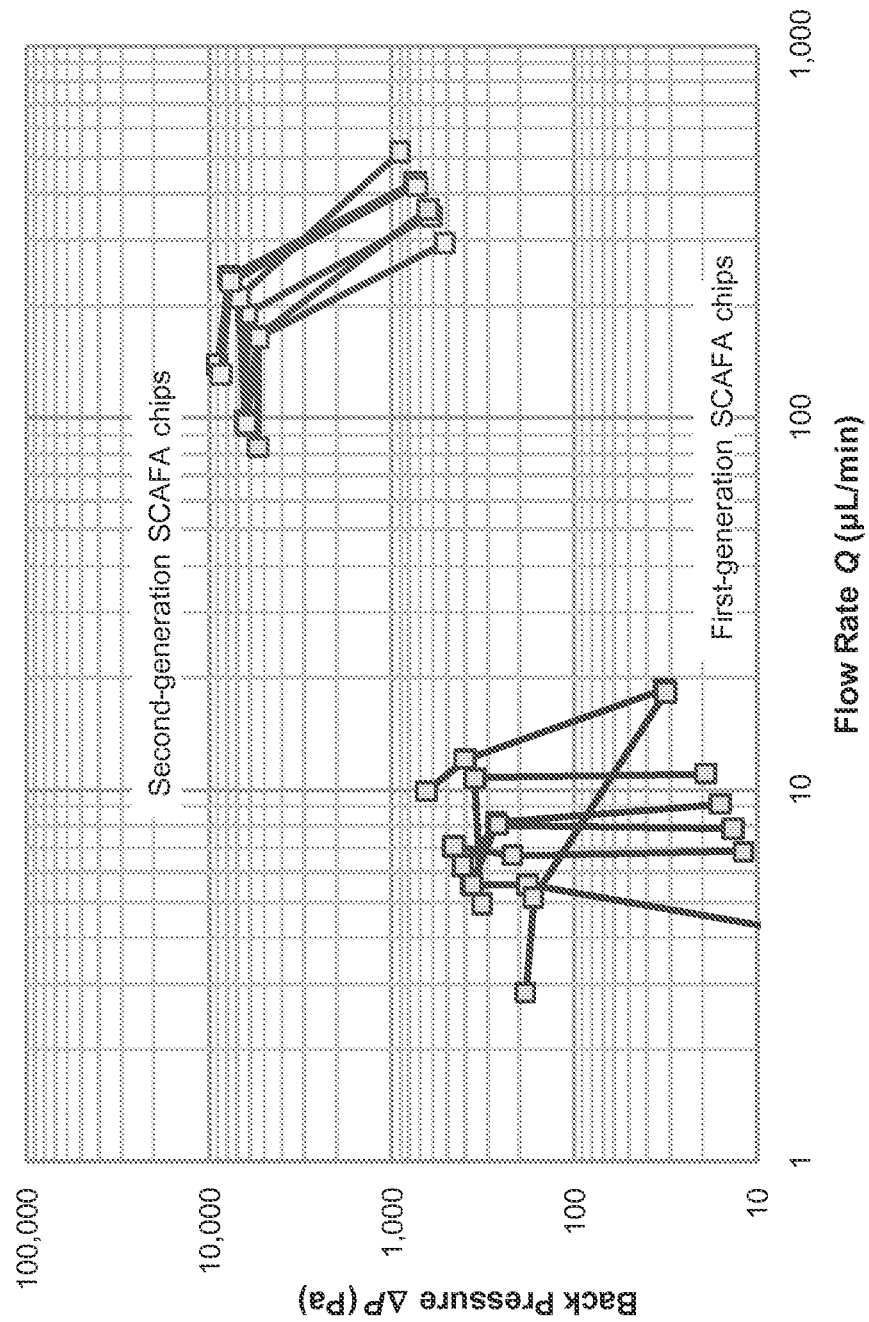
FIG. 13 illustrates the back pressure and flow rate among first and second generation microfluidic actuators, according to one embodiment of the invention.

FIG. 13 illustrates the back pressure and flow rate among first and second generation microfluidic actuators, according to one embodiment of the invention.

Figure 14:
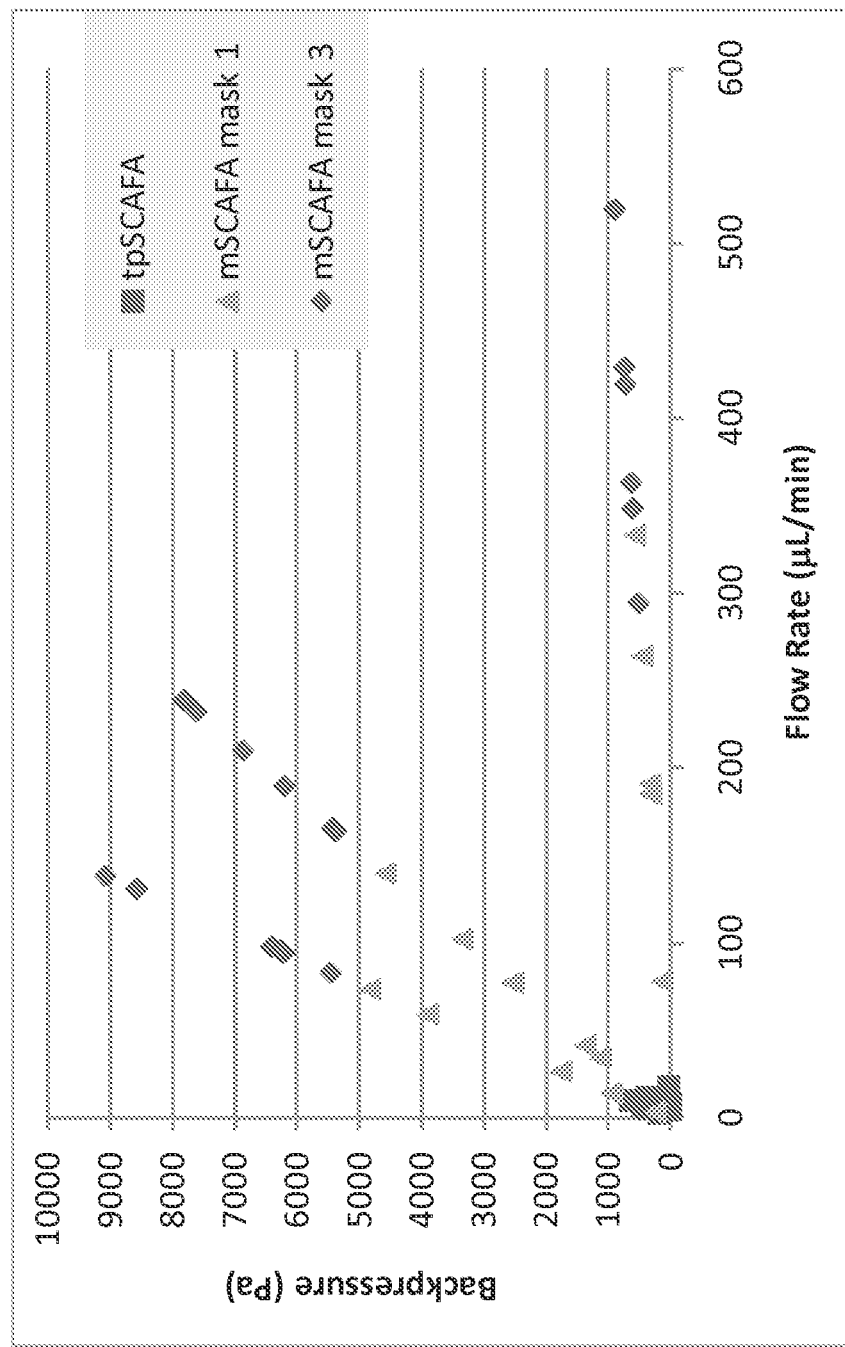
FIG. 14 illustrates the back pressure and flow rate among various microfluidic actuators, according to one embodiment of the invention.

FIG. 14 illustrates the back pressure and flow rate among various microfluidic actuators, according to one embodiment of the invention.

Figure 15:
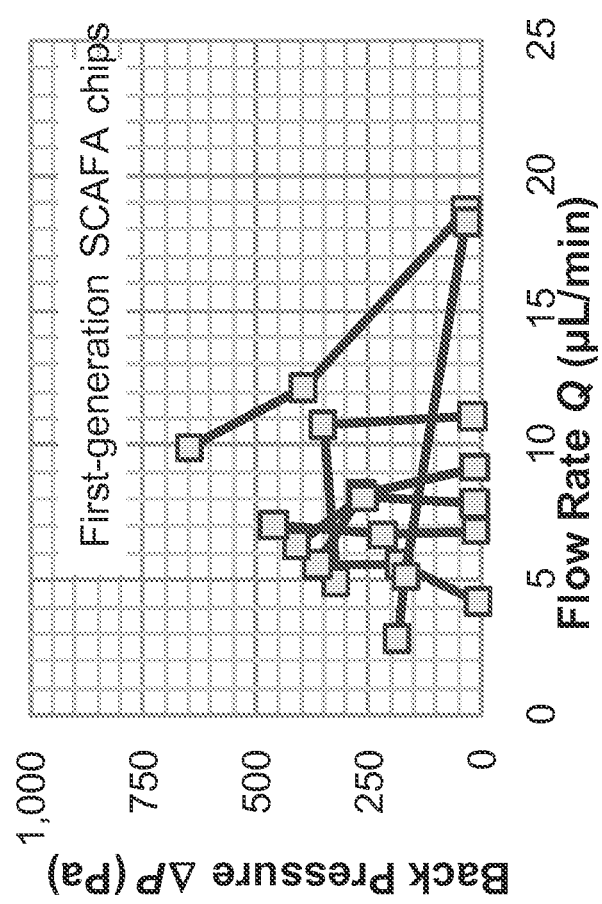
FIG. 15 illustrates back pressure and flow rate among first generation microfluidic actuators, according to one embodiment of the invention.

FIG. 15 illustrates back pressure and flow rate among first generation microfluidic actuators, according to one embodiment of the invention.

Figure 16:
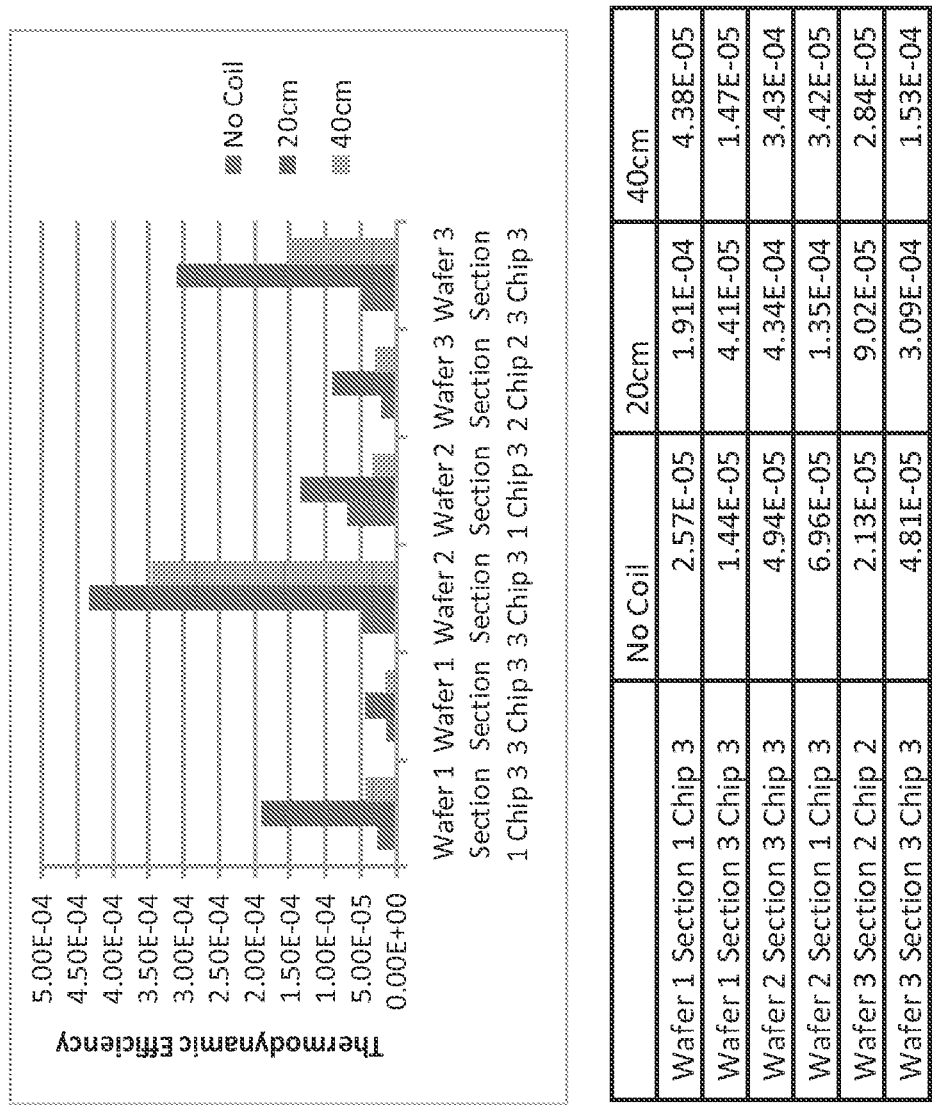
FIG. 16 shows the thermodynamic efficiencies of various microfluidic actuators of the invention, according to one embodiment of the invention.

FIG. 16 shows the thermodynamic efficiency of microfluidic actuators of the invention, according to one embodiment of the invention.

Figure 17:
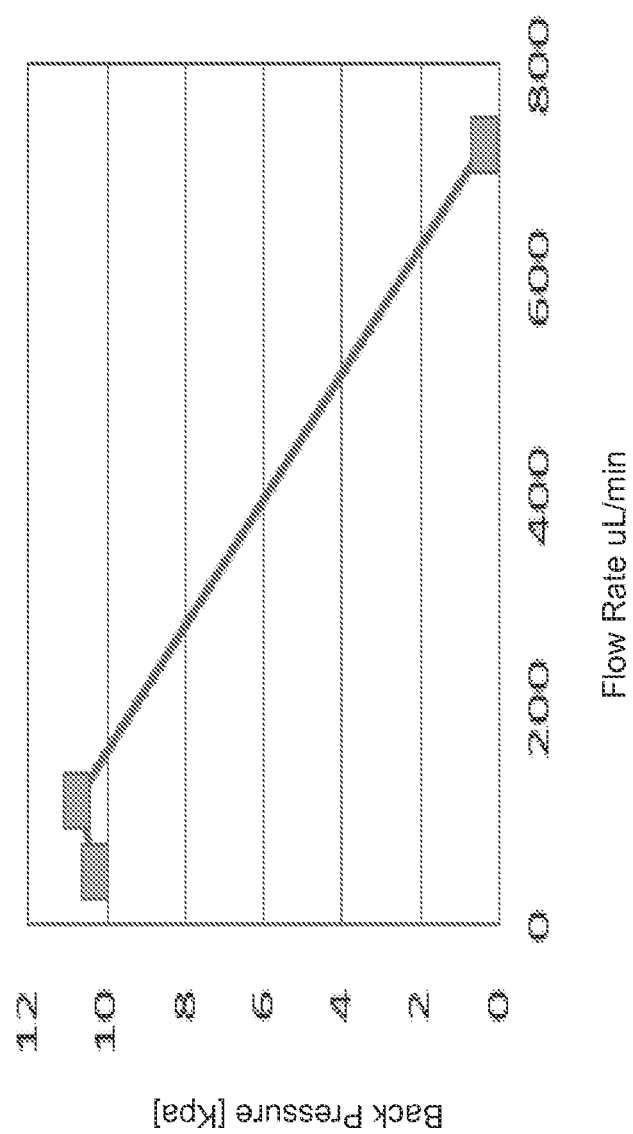
FIG. 17 illustrates the back pressure and flow rate for a 1 mm×3 mm microfluidic actuator (e.g., a Slit Capillary Array Fluidic Actuator (SCAFA)) using laser-cut, platinum-plated electrodes, according to one embodiment of the invention.
Figure 18A:
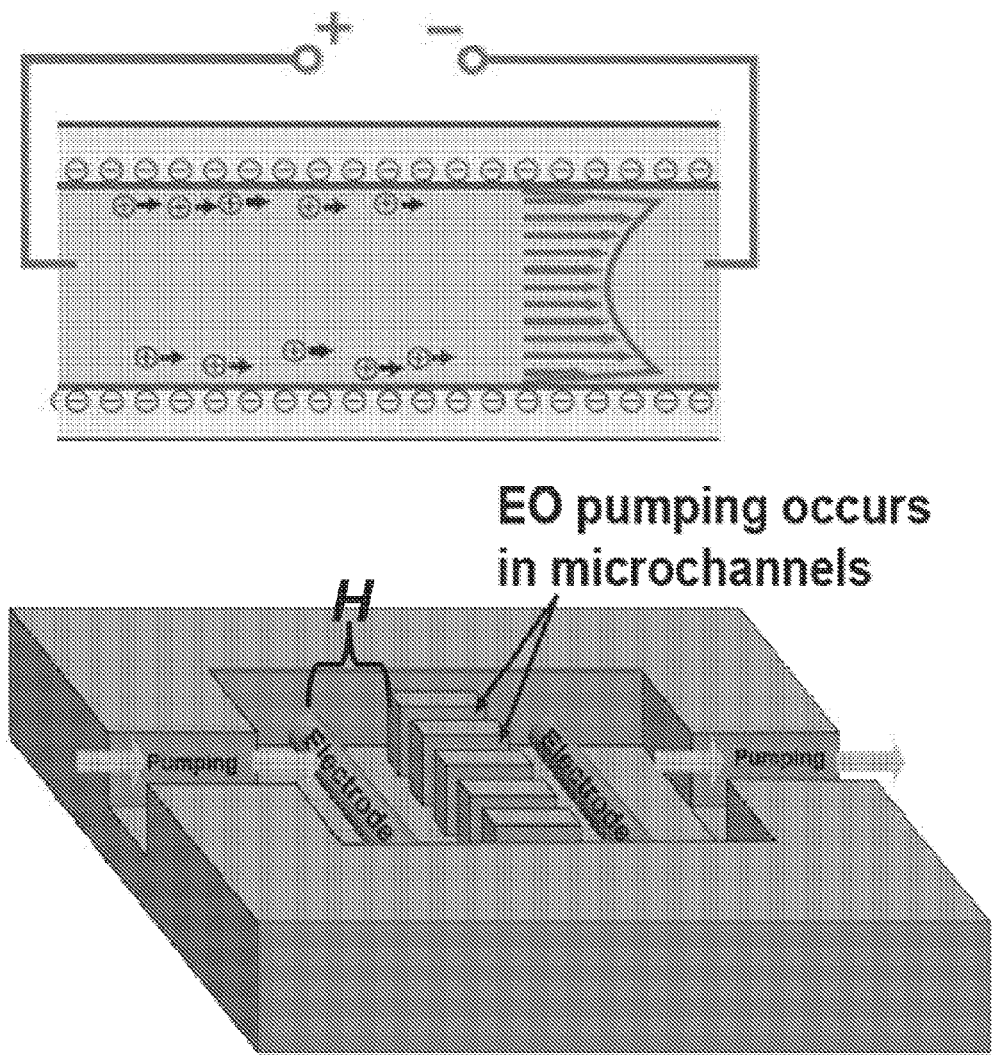
FIGS. 18A-C illustrate the electric field effects in microfluidic actuators of the invention (SCAFAs), according to one embodiment of the invention.
Figure 18B:
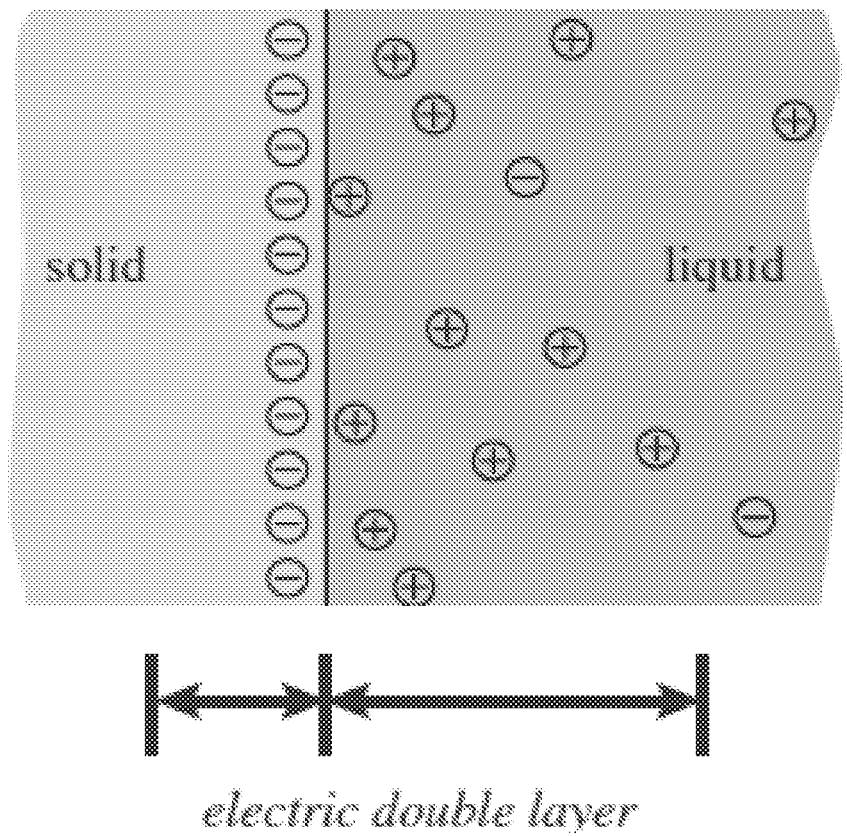
Figure 18C:
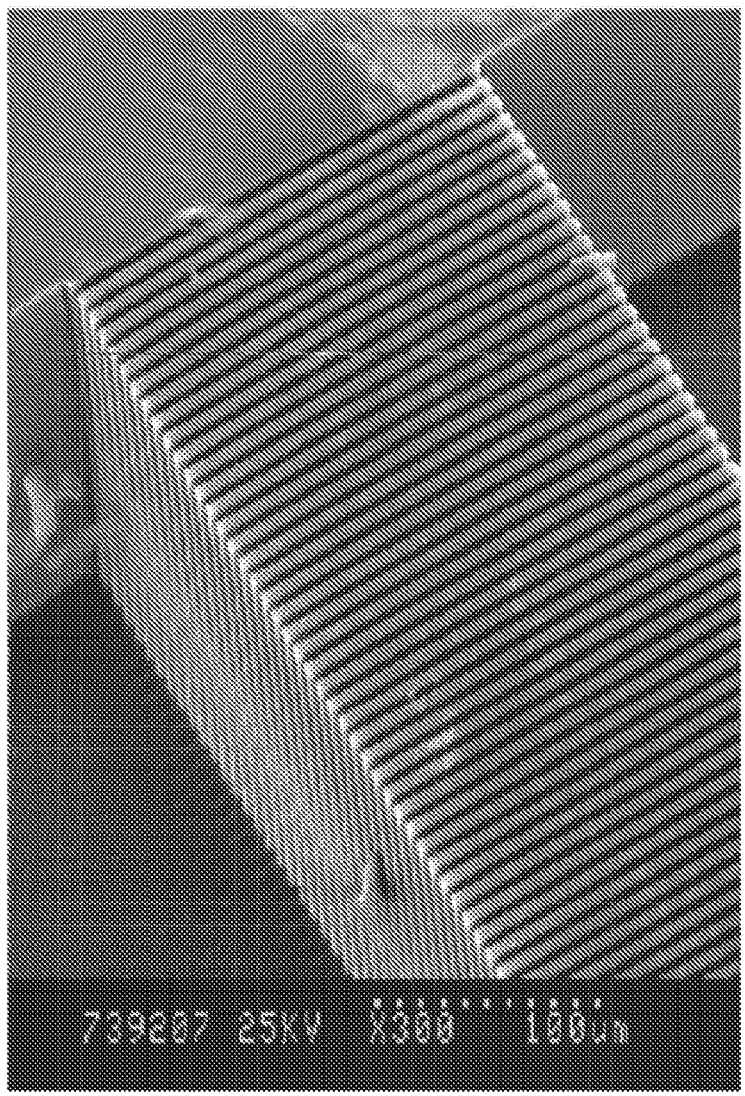

FIG. 17 illustrates the back pressure and flow rate for a 1 mm×3 mm microfluidic actuator (SCAFA) using laser-cut, platinum-plated electrodes, according to one embodiment of the invention. The process for development of laser-cut, platinum-plated electrodes is as follows:

1) Laser cut a 25-micron thick stainless steel sheet to electrode pattern, but held captive in a sheet with ligatures
2) Gold "strike" or "flash" the stainless steel sheet, proving a gold adhesion layer less than 0.1 micron thick.
3) Electroplate 1-2 microns of platinum on top of the gold
4) Separate the individual electrodes from the sheet manually
5) Laser cut adhesive-backed polyimide to the required insulation area
6) Encapsulate the electrodes between the two polyimide insulators FIGS. 18A-C illustrate the electric field effects in microfluidic actuators of the invention (Slit Capillary Array Fluidic Actuators (SCAFAs)), according to one embodiment of the invention. The electro-osmotic field (EOF) is associated with the action of an externally imposed electric field on the mobile ions of the fluid phase of the electric double layer. Viscous effects result in bulk flow. In SCAFAs, the bulk flow generated within an internal high field zone creates piston-like action on fluid phases outside the actuatory chip. The high-field zone is designed for efficient EOF generation through choice of surface chemistry optimization and geometry. A parallel arrangement of narrow, deep, closely spaced microchannels—referred to as a slit capillary array—formed in single-crystal silicon wafer using photolithography tools can be readily optimized for EOF (Laser, 2006). A common slit capillary array design is shown in FIG. 18A. EOF in a slit capillary can be modeled using parallel-plate flow assumptions (Burgreen and Nakache 1964). For a slit of width 2a, length 1l, the general relationship between average velocity v in the slit and the end to end pressure differential Δp is:

$$\bar{v} = -\frac{a_1^2}{3\mu l_s}\Delta p_1 + \frac{\varepsilon\zeta}{\mu}E_x[1 - G(\alpha, \kappa a_1)]$$

where μ is the fluid viscosity, μ is the fluid permittivity, $E_x$ is the axial electric field, and ζ is the zeta potential (an empirical parameter related to the double layer thickness and charge distribution). Maximizing $E_x$ for a given applied voltage therefore is an important tool for optimizing both pressure and flow rate performance.

FIG. 18A shows an externally applied electric field can result in bulk fluid motion against a pressure gradient as mobile ions in the fluid phase of the double layer (Laser and Santiago, 2004). The figure shows a schematic of a microfluidic actuator (SCAFA) with inlets, microchannels and electrodes at a height (H) separating them.

FIG. 18B shows a schematic representation of electric double layer (EDL) formation at a fluid-solid interface. Counter ions in the liquid accumulate in the vicinity of the charged surface.

FIG. 18C shows a SEM image of the microchannels inside a microfluidic actuator (SCAFA), according to an embodiment of the invention.

Figure 19:
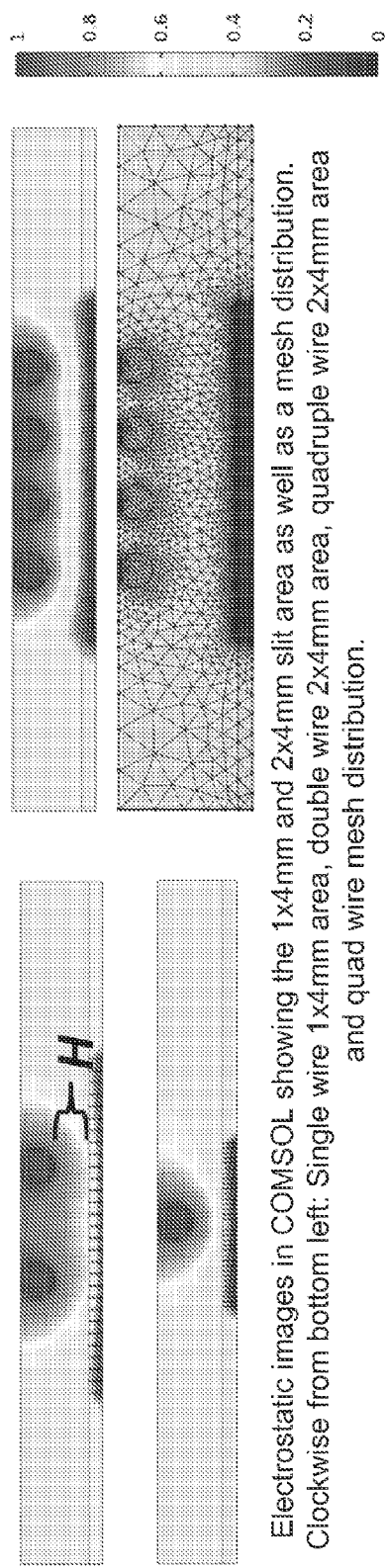
FIG. 19 illustrates modeling of microfluidic actuators of the inventon (SCAFAs), according to one embodiment of the invention.

In a typical SCAFA design, EOF is generated within a set of parallel microchannels with approximately rectilinear geometry and minimal microchannel-to-microchannel variation. Numerical simulation is an important tool for optimizing SCAFA design with a minimal number of expensive, labor intensive fabrication iterations. COMSOL Inc.'s electrostatic modeling capabilities were used to study the effect of electrode geometry and position on the average $E_x$ across a variety of slit capillary array designs. Single, double and quadruple platinum electrodes were simulated in an aqueous environment assuming fluid properties consistent with typical SCAFA working fluids. The simulated slit patterns matched the various geometries of the SCAFA designs and a parametric investigation on the electrode height (H) above the slits and lateral distance from the center was performed. FIG. 19 shows electrostatic images in COMSOL showing the 1×4 mm and 2×4 mm slit area as well as mesh distribution (Clockwise from bottom left: single wire 1×4 mm area, double wire 2×4 mm area, quadruple wire 2×4 mm area, and quad wire mesh distribution).

FIGS. 20A-D illustrate additional data from a COMSOL parametric study on flow rate and pressure performance using various electrode configurations, according to one embodiment of the invention. The monotonic decrease in field strength with increasing H is both qualitatively and quantitatively consistent with one-dimensional electrical resistance models for ionic current in the fluid phase. However the pronounced dependence on $E_x$ on multielectrode configuration, particularly at small H, is poorly modeled by simple resistor networks. The simulation indicates that a judicious choice of electrode geometry—such as the quad electrode configuration described above—can markedly improve SCAFA flow rate and pressure performance.

Figure 20A:
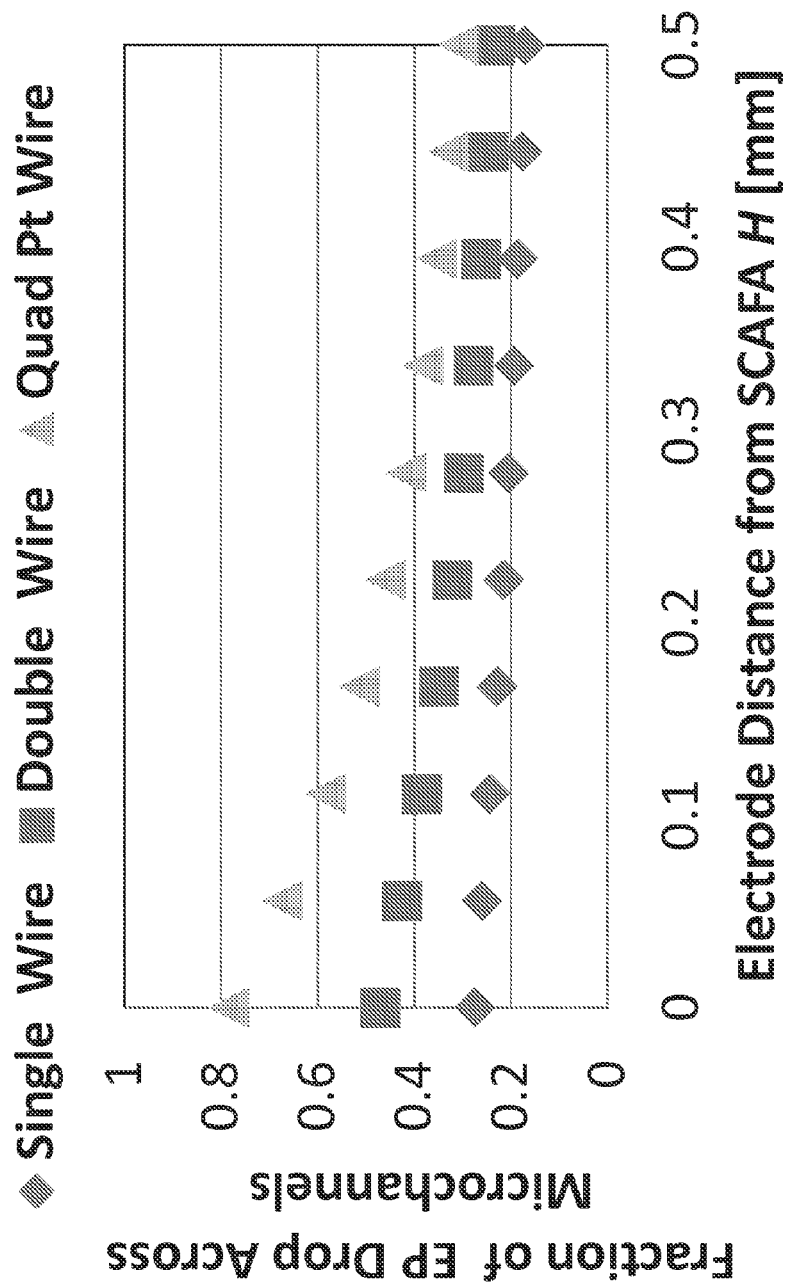
FIGS. 20A-D illustrates additional studies on flow rate and pressure performance using various electrode configurations, according to one embodiment of the invention.
Figure 20B:
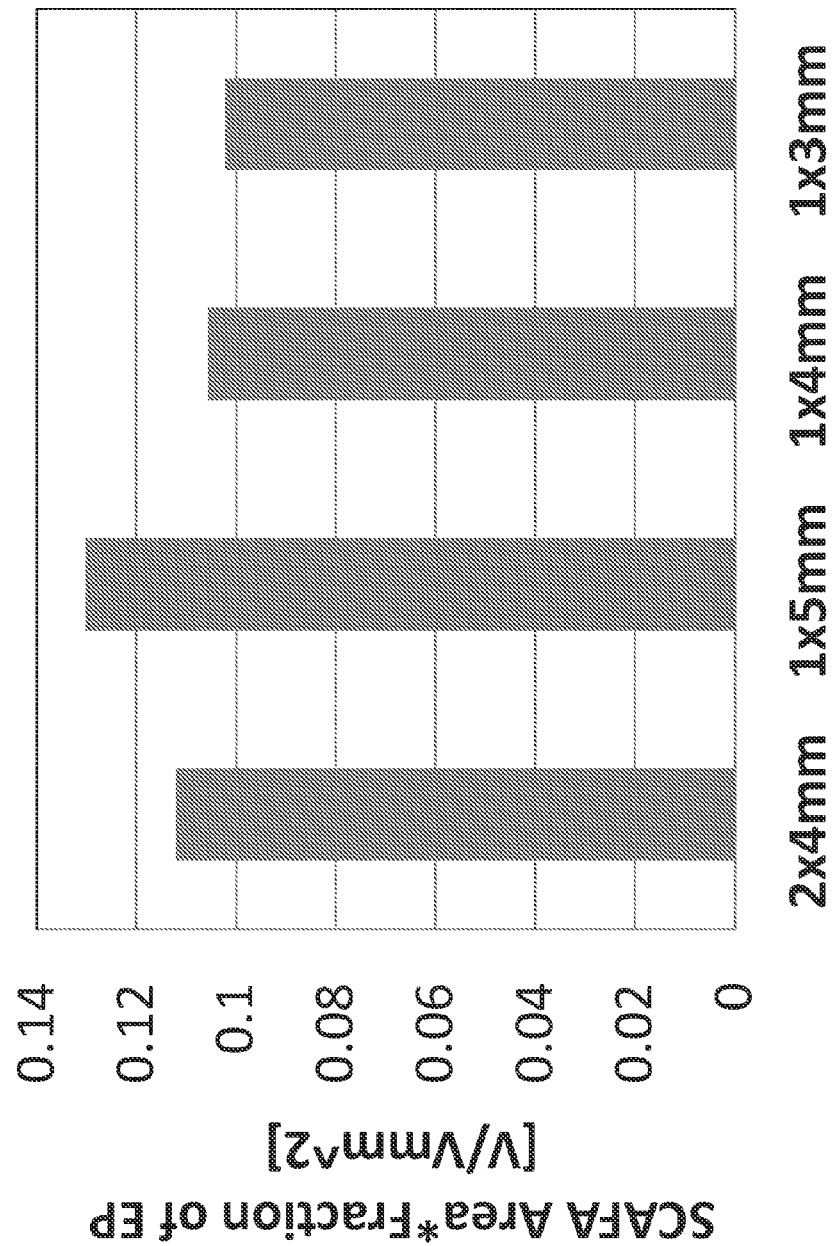

FIG. 20A illustrates the fraction of axial electric potential (EP) drop across the slits in the 2×4 mm slit area SCAFA for single, double, and quadruple electrods versus the height (H) of the electrode above the SCAFA surface. FIG. 20B illustrates the fraction of electric potential drop across the slits multiplied by the respective slit area vs. SCAFA design.

Figure 20C:
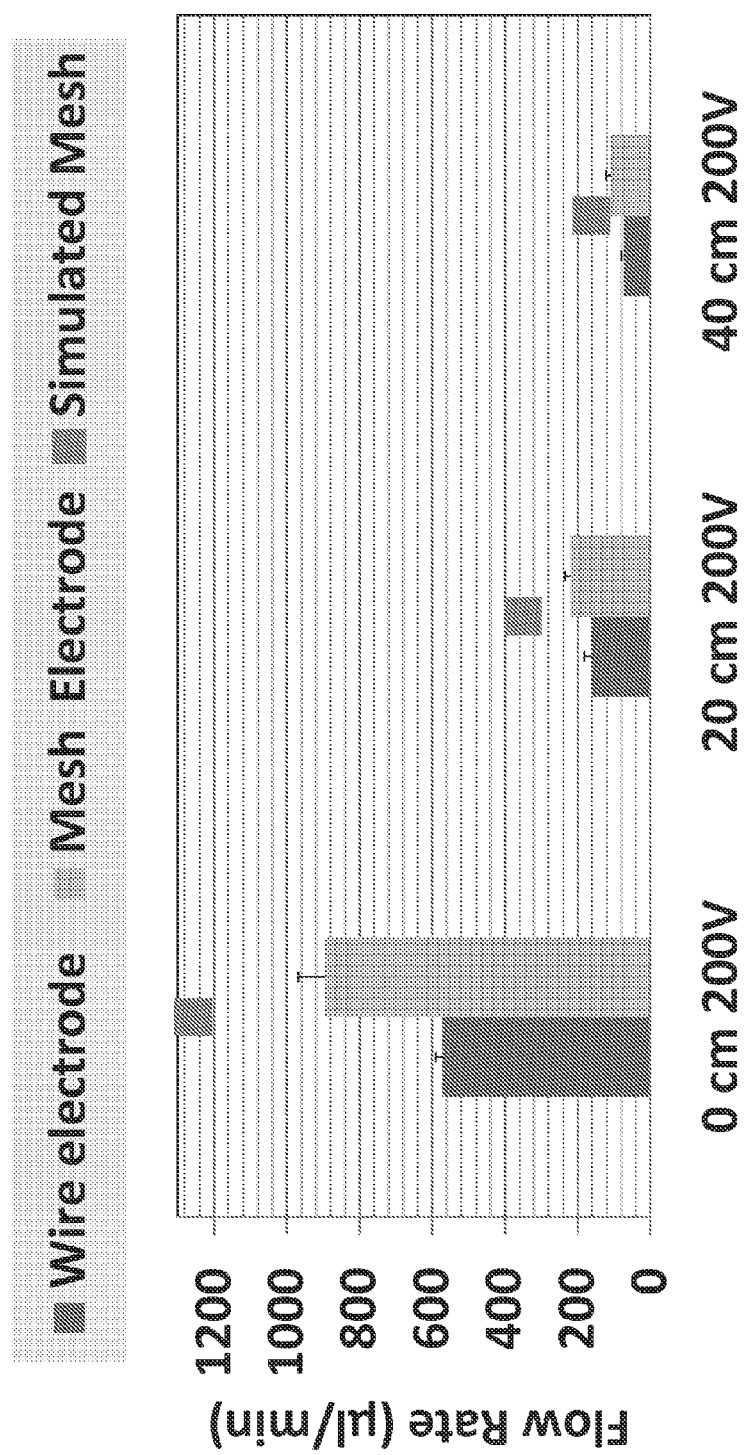
Figure 20D:
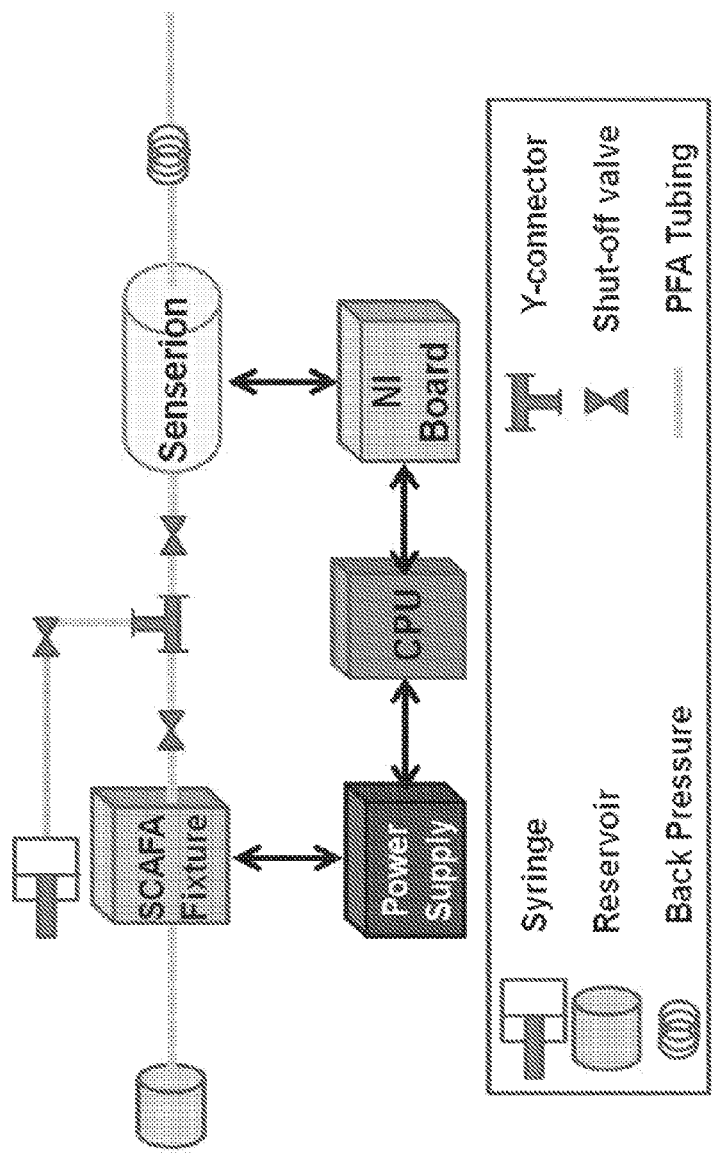

To test COMSOL model predictions, SCAFAs were tested with a variety of electrode configurations. The experimental setup and key results are shown in FIGS. 20C and 20D. The applied potential is 200 volts and the SCAFAs have 2×4 mm flow zones. A single wire is the base case. A wire mesh electrode approximated the quad electrode geometry. The flow rate of each triplicate experiment was measured with a Senserion flow meter at 3 relative back pressures. Back pressures were generated by attaching a 0.5 mm diameter coil at 2 lengths inline with the flow path. FIG. 20C shows a measured flow rate of a 2×4 mm slit area SCAFA with a single wire and wire mesh electrode under three back pressure conditions. Simulated mesh values are calculated from measured SCAFA flow rates with wire electrode multiplied by the simulated quad wire improvement. FIG. 20D shows a schematic of the experimental set up used to perform the experiments.

Example 3: Applications

The microfluidic device may be used for a wide variety of applications in human health, animal health, food safety, and environmental monitoring involving transport of small amounts of fluids.

Examples of such applications include the movement of fluids containing samples and reagents for measurement of target species in body fluids, such as diagnosis of infectious and non-infectious disease through detection and quantification of a variety of DNA, RNA, proteins, or other categories of target molecules in tissue samples from patients.

The microfluidic device may be used in a cartridge to transport or mix fluids containing samples and reagents for the measurement of a target species in environmental samples, such as the detection of chemical or biological contaminants or other materials of interest.

The microfluidic device may also be used in a cartridge to transport or mix fluids containing samples and reagents for measurement of target species in food samples, such as detection of toxic substances or other materials of interest.

The microfluidic device may also be used in a cartridge to transport reactants of a chemical synthesis process. For example, two chemical compounds could be combined to produce a compound of pharmaceutical relevance.

The microfluidic device may be used to transport a material that is toxic or otherwise poorly suitable for direct human handling. For example, pipetting of solutions is associated with risk of aerosolization, which could pose risk of infection to people in the vicinity if the solution contains airborne-transmissible pathogens. The microfluidic device can be used to eliminate a pipetting step.

The microfluidic device may also be used to reconstitute a material from a dried-down or lyophilized form into a solution form. The microfluidic device can transport a reconstituting solution, such as an aqueous, within a microchannel network to a location where the dried-down or lyophilized material, such as an enzyme, is held. The reconstitution process can include causing the aqueous to flow over the lyophilized material. The reconstitution process can include subjecting the flow to oscillatory or other action to speed reconstitution through disruption of concentration gradients relative to an unperturbed state.

Other areas of application include drug delivery and other medicinal applications. Various other areas of application include the transport of fluids in miniature power systems, such as fuel cells and solar sterling engines; endoscopic sampling and/or catheter-based sampling; wound care; and use in nebulizers.

Examples of use of the microfluidic device of the invention in a cartridge are described in U.S. Provisional Application No. 61/771,708, filed on Mar. 1, 2013, which is hereby incorporated in its entirety by reference.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

[1] F. Yeaple, *Fluid Power Design Handbook, Third Edition*. CRC Press, 1995.

[2] R. J. Hunter, *Zeta Potential in Colloid Science: Principles and Applications*. Academic Press, 1981.

[3] S. Zeng, C.-H. Chen, J. G. Santiago, J.-R. Chen, R. N. Zare, J. A. Tripp, F. Svec, and J. M. Fréchet, "Electroosmotic flow pumps with polymer frits," *Sensors and Actuators B: Chemical*, vol. 82, no. 2-3, pp. 209-212, February 2002.

[4] S. Yao and J. G. Santiago, "Porous glass electroosmotic pumps: theory," *J Colloid Interface Sci*, vol. 268, no. 1, pp. 133-142, December 2003.

[5] P. H. Paul, D. J. Rakestraw, D. W. Arnold, K. R. Hencken, J. S. Schoeniger, and D. W. Neyer, "Electrokinetic high pressure hydraulic system," U.S. Pat. No. 6,277,257 21 Aug. 2001.

[6] Chuan-Hua Chen and J. G. Santiago, "A planar electroosmotic micropump," *J. Microelectromech. Syst.*, vol. 11, no. 6, pp. 672-683, December 2002.

[7] D. J. Laser, "Design, Fabrication, and Applications of Slit Capillary Array Electroosmotic Micropumps," Stanford University, Stanford, Calif., 2005.

[8] J. Frey, A. Droitcour, and D. Laser, "Modeling Electric Fields in Slit Capillary Array Fluidic Actuators with Complex Electrode Geometries," presented at the COMSOL User Conference, 2012.

[9] S. Yao, A. M. Myers, J. D. Posner, K. A. Rose, and J. G. Santiago, "Electroosmotic Pumps Fabricated From Porous Silicon Membranes," *J. Microelectromech. Syst.*, vol. 15, no. 3, pp. 717-728, June 2006.

[10] R. F. Probstein, *Physicochemical Hydrodynamics: An Introduction*. John Wiley & Sons, 2005.

[11] D. Burgreen and F. R. Nakache, "Electrokinetic Flow in Ultrafine Capillary Slits 1," *The Journal of Physical Chemistry*, vol. 68, no. 5, pp. 1084-1091, 1964.

[12] M. J. Madou, *Fundamentals of Microfabrication: The Science of Miniaturization, Second Edition*. CRC Press, 2002.

R. J. Hunter, "Zeta Potential in Colloid Science," San Diego: Academic Press, Inc., 1981.

D. Burgreen and F. R. Nakache, "Electrokinetic Flow in Ultrafine Capillary Slits," *J Phys. Chemistry*, vol. 68, pp. 1084-1091, 1964.

D. J. Laser, A. M. Myers, S. Yao, K. F. Bell, K. E. Goodson, J. G. Santiago, and T. W. Kenny, "Silicon Electroosmotic Micropumps for IC Thermal Management," Proc. 12th International Conference on Solid-State Sensors, Actuators and Microsystems (Transducers '03), Boston, Mass., Santiago/Stanford D. J. Laser, "Temporal Modulation of Electroosmotic Micropumps," Proc. ASME IMECE, Fluids Engineering in Micro- and Nano-Systems VII, 2006: p. 13960.

The invention claimed is:

1. A device comprising:
a slat structure comprising a rigid structural frame supporting a plurality of approximately evenly spaced slats, such slats having a thickness, and wherein said slat structure comprises a plurality of interstices between said slats and said plurality of interstices comprise a plurality of fluid passageways extending through said thickness such that a fluid is capable of flowing through said slat structure, wherein each of said plurality of interstices has an in-plane dimension a and a second in-plane dimension b, wherein said dimension a is between 1 and 10 microns and said dimension b is at least the lesser of fifty times greater than said dimension a of said interstice or 250 microns; and the number of interstices is at least ten;
a housing enclosing said slat structure, comprising:
a first structure defining a first fluid cavity adapted for housing a fluid and in fluidic communication with a first side of said interstices;
a second structure defining a second fluid cavity adapted for housing a fluid and in fluidic communication with a second side of said interstices, wherein said first fluid cavity, said plurality of interstices in said slat structure, and said second fluid cavity define a fluid pathway, wherein a lowest flow resistance path from said first fluid cavity to said second fluid cavity is through said plurality of interstices; and
a plurality of electrodes for generating an electric field within said plurality of interstices.

2. The device of claim 1, wherein said slat structure, said housing, and said plurality of electrodes are configured such that, during operation, at least ⅔ of a maximum voltage difference $\Delta V$ applied across said plurality of electrodes occurs between said first and second sides of said slat structure.

3. The device of claim 1, wherein said slat structure is composed of an insulating material or a semi-conducting core material with surface coatings.

4. The device of claim 1, wherein an average electrical resistivity of a primary structural material composing the slat structure is at least 1000 ohm-centimeters.

5. The device of claim 1, wherein, with an electrical potential difference applied across said electrodes, an electric field arises within some or all of said plurality of interstices, and wherein, in each of said plurality of interstices where an electric field arises, a component of said electric field is parallel to at least some of the walls of said interstice.

6. The device of claim 1, wherein said dimension b is greater than or equal to 0.5 mm.

7. The device of claim 1, wherein the sidewalls of the slats are straight.

8. The device of claim 1, wherein the sidewalls of the slats are curved, sawtoothed, wavy, or otherwise non-rectilinear.

9. The device of claim 1, wherein said thickness of said slats is between 50 microns and 2 mm in length.

10. The device of claim 1, wherein said dimension a is between 0.5 and 10 microns.

11. The device of claim 1, wherein said slat structure is predominantly silicon.

12. The device of claim 1, wherein said slat structure is coated with one or more insulating thin films.

13. The device of claim 12, wherein said thin film comprises a nitrogen-containing silicon material or silicon oxide.

14. The device of claim 1, wherein said slat structure comprises crystalline silicon.

15. The device of claim 14, wherein said slat structure comprising crystalline silicon has a resistivity of at least 1000 ohm-centimeters.

16. The device of claim 1, wherein said plurality of interstices is approximately uniform in size and shape.

17. The device of claim 1, wherein said plurality of interstices is approximately uniform in its smaller cross-sectional dimension.

18. The device of claim 1, wherein said plurality of interstices collectively forms a flow passageway in which all in-plane dimensions are within a factor of five of one another.

19. The device of claim 1, further comprising a volume of aqueous solution in said housing, said volume extending at least 100 microns into said first and second fluid cavities on either side of said slat structure.

20. The device of claim 1, wherein said plurality of electrodes are composed of stainless steel meshes with electroplated platinum.

21. The device of claim 1, further comprising a battery or other electrical potential source connected to said plurality of electrodes.

22. The device of claim 21, further comprising a signal generator and associated hardware for varying the electrical potential applied to said plurality of electrodes as a sine wave or arbitrary waveform.

23. The device of claim 1, further comprising a battery or other electrical potential source with a switching mechanism for periodically turning on and off the voltage applied across said plurality of electrodes.

24. The device of claim 23, wherein said voltage pulse frequency is 0.5 Hz or faster, 1.0 Hz or faster, 10 Hz or faster, or 100 Hz or faster.

25. The device of claim 1, wherein a surface of said slat structure in said plurality of interstices is capable of increasing an absolute value of a zeta potential at an interface of said fluid and said slat structure.

26. The device of claim 1, wherein said device has a fluid power generation capacity of at least 10-8 watts.

27. The device of claim 1, wherein said device is capable of sustaining power for at least 30 seconds.

28. The device of claim 1, wherein said device has a response time for power generation is less than 10 seconds.

29. The device of claim 1, wherein said dimension a is the same for each of said plurality of interstices.

30. A method of manufacturing a fluidic device, comprising:
generating a slat structure having a first face and a second face, wherein a separation between said first and second faces of said slat structure defines a thickness and wherein a fluid is capable of flowing through a plurality of interstices in said slat structure, wherein each of said plurality of interstices has a dimensions a and b across said face of said interstice, wherein said dimension b is between 50 microns and 2 mm in length, and is at least fifty times greater than dimension a of said interstice, and wherein the average electrical resistivity across said slat structure is at least 1000 ohm-centimeters;
generating a housing enclosing said slat structure, comprising:
a first structure defining a first fluid cavity adapted for housing a fluid and in fluidic communication with one face of said slat structure;
a second structure defining a second fluid cavity adapted for housing a fluid and in fluidic communication with the other face of said slat structure, wherein said first fluid cavity, said plurality of interstices and said second fluid cavity define a fluid pathway, wherein a lowest flow resistance path from said first fluid cavity to said second fluid cavity is through said plurality of interstices; and providing a plurality of electrodes for generating an electric field within said plurality of interstices.

31. The method of claim 30, wherein said slat structure, said housing and said plurality of electrodes are configured such that at least ⅔ of a maximum voltage difference $\Delta V$ applied to said plurality of electrodes occurs between said first face and said second face of the slat structure.

32. The method of claim 30, further comprising adding a conformal insulating layer to at least one surface of said slat structure to minimize the flow of electrical current between said fluid and said slat structure.

33. The method of claim 30, further comprising adding a conformal insulating layer to at least one surface of the slat structure to maximize an absolute value of a zeta potential at an interface of said fluid and the interior surfaces of said interstices.

34. The method of claim 30, wherein said electric field has a component parallel to the walls of said interstices.

35. The method of claim 30, further comprising coating said slat structure with one or more thin films of silicon.

36. The method of claim 35, wherein said thin film comprises silicon oxide.

37. The method of claim 30, further comprising coating said slat structure with one or more thin films of silicon nitride.

38. The method of claim 30, wherein said slat structure comprises crystalline silicon.

39. The method of claim 38, wherein said crystalline silicon has a resistivity of at least 1000 ohm-centimeters.

40. The method of claim 30, wherein said dimension a is between 0.5 and 10 microns.

41. The method of claim 30, wherein said slat structure is produced by:

photolithographically patterning a plurality of slat structures on a crystalline silicon wafer;

etching said plurality of interstices through bombardment with directional ions;

removing a photolithography process residue; and dicing said wafer into individual slat structures.

42. The method of claim 41, further comprising thinning said wafer prior to dicing by means of a chemical-mechanical polishing process.

43. The method of claim 30, further comprising providing a volume of aqueous solution in said housing, said volume extending at least 100 microns into said first and second fluid cavities on either side of said slat structure.

44. The method of claim 30, further comprising connecting said plurality of electrodes to an electrical potential source.

45. The method of claim 44, further comprising programming a switching apparatus such as a pulse generator to deliver a periodic pattern of voltage pulses to said plurality of electrodes.

46. The method of claim 44, wherein said pattern of voltage pulses repeats at a frequency of 0.5 Hz or faster, 1.0 Hz or faster, 10 Hz or faster, or 100 Hz or faster.

47. The method of claim 44, wherein the fluid power output is controlled by the duty cycle of said pulses.

48. The method of claim 47, wherein said duty cycle is between 1 and 90%.

49. The method of claim 47, wherein said pulse duration is shorter than a period of time corresponding to a 1/pattern repeat frequency.

* * * * *